US009222059B2

(12) United States Patent
Germain et al.

(10) Patent No.: US 9,222,059 B2
(45) Date of Patent: Dec. 29, 2015

(54) CLEANING FORMULATIONS WITH IMPROVED SURFACTANT SOLUBILITY AND METHODS OF PRODUCTION AND USE THEREOF

(71) Applicant: The Sun Products Corporation, Wilton, CT (US)

(72) Inventors: Adam W. Germain, Naugatuck, CT (US); Calogero A. DiStefano, Milford, CT (US); Guanglin Sun, Branchburg, NJ (US); Charles Crawford, Southbury, CT (US); Igor Anisimov, Quaker Hill, CT (US); Robert M. Doris, Trumbull, CT (US)

(73) Assignee: The Sun Products Corporation, Wilton, CT (US)

( * ) Notice: Subject to any disclaimer, the term of this patent is extended or adjusted under 35 U.S.C. 154(b) by 29 days.

(21) Appl. No.: 13/623,473

(22) Filed: Sep. 20, 2012

(65) Prior Publication Data

US 2013/0072410 A1 Mar. 21, 2013

Related U.S. Application Data

(60) Provisional application No. 61/536,887, filed on Sep. 20, 2011.

(51) Int. Cl.
| | | |
|---|---|---|
| *C11D 1/12* | (2006.01) | |
| *C11D 1/75* | (2006.01) | |
| *C11D 1/83* | (2006.01) | |
| *C11D 3/34* | (2006.01) | |
| *C11D 17/04* | (2006.01) | |
| *C11D 3/30* | (2006.01) | |
| *C11D 11/00* | (2006.01) | |
| *A61Q 19/10* | (2006.01) | |
| *A61K 8/40* | (2006.01) | |
| *A61K 8/46* | (2006.01) | |
| *A61Q 5/02* | (2006.01) | |
| *C11D 1/28* | (2006.01) | |

(52) U.S. Cl.
CPC ... *C11D 1/83* (2013.01); *A61K 8/40* (2013.01); *A61K 8/466* (2013.01); *A61Q 19/10* (2013.01); *C11D 1/12* (2013.01); *C11D 1/123* (2013.01); *C11D 3/30* (2013.01); *C11D 3/34* (2013.01); *C11D 11/0011* (2013.01); *C11D 11/0017* (2013.01); *C11D 11/0023* (2013.01); *C11D 17/043* (2013.01); *A61Q 5/02* (2013.01); *C11D 1/28* (2013.01); *C11D 1/75* (2013.01)

(58) Field of Classification Search
CPC ............ C11D 1/12; C11D 1/123; C11D 1/75; C11D 17/043; C11D 11/0011; C11D 11/0017; C11D 11/0023; C11D 3/30; C11D 3/34; C11D 3/3409
USPC ......... 510/125, 127, 130, 136, 137, 138, 221, 510/336, 337, 350, 351, 357, 503, 237, 238, 510/427
See application file for complete search history.

(56) References Cited

U.S. PATENT DOCUMENTS

| | | | |
|---|---|---|---|
| H1635 | H | 3/1997 | Vander Meer |
| 5,698,046 | A | 12/1997 | St. Laurent et al. |
| 6,764,989 | B1 | 7/2004 | Huish et al. |
| 2004/0063598 | A1* | 4/2004 | Riebe et al. ............ 510/293 |
| 2008/0070821 | A1 | 3/2008 | Huish et al. |
| 2008/0070822 | A1 | 3/2008 | Huish et al. |
| 2010/0240569 | A1 | 9/2010 | Boutique et al. |
| 2010/0275396 | A1 | 11/2010 | Nakano et al. |

OTHER PUBLICATIONS

International Search Report for International Application No. PCT/US12/56282, US Patent and Trademark Office, United States, mailed on Nov. 30, 2012.

* cited by examiner

*Primary Examiner* — Gregory R Delcotto
(74) *Attorney, Agent, or Firm* — Sterne, Kessler, Goldstein & Fox PLLC

(57) ABSTRACT

The present invention provides liquid cleaning compositions useful in cold water and hard water laundry applications, and methods for making and using such compositions. The compositions of the invention use surfactants or surfactant blends, such as α-sulfofatty acid esters or mixtures thereof (optionally along with one or more additional components), that have increased solubility/stability at cold temperatures, at higher-than-usual concentrations, and/or in hard water, with the composition remaining as a clear liquid. In certain embodiments, the compositions of the invention may be provided in the form of a unit dose, for example in a water-soluble pack or pouch. In use, the compositions of the invention result in an enhanced detergency along with a reduced amount of residue remaining in the machine, on laundered garments or cleaned dishware or hard surfaces, and on the body in personal care settings, and demonstrate a longer shelf-life, particularly when stored or used in colder temperatures.

39 Claims, 11 Drawing Sheets

CLEANING FORMULATIONS WITH IMPROVED SURFACTANT SOLUBILITY AND METHODS OF PRODUCTION AND USE THEREOF

CROSS REFERENCE TO RELATED APPLICATIONS

The present application claims the benefit of the filing date of U.S. Provisional Application No. 61/536,887, filed Sep. 20, 2011, the contents of which are incorporated herein by reference in their entirety.

BACKGROUND OF THE INVENTION

1. Field of the Invention

The present invention is in the general field of chemistry and surfactant formulation, and household cleaning methods. More specifically, the present invention provides to liquid cleaning compositions useful in cold water and hard water cleaning applications, and methods for making and using such compositions. The compositions of the invention, which are useful in various household cleaning applications including laundry, dish, hard surface and personal care cleaning, use surfactants and surfactant blends (optionally along with one or more additional components) that have increased solubility/stability at cold temperatures, at higher-than-usual concentrations, and/or in hard water, with the composition remaining as a clear liquid. In use, the compositions of the invention result in an enhanced detergency along with a reduced amount of residue remaining in the machine, on laundered garments or cleaned dishware or hard surfaces, and on the body in personal care settings, and demonstrate a longer shelf-life, particularly when stored or used in colder temperatures.

2. Related Art

Detergents have been used for many years in a variety of household care settings, such as in laundry settings to clean clothing and other fabric materials, to clean dishware or hard surfaces, and in personal care settings such as hair shampoos and body washes. Detergents originally contained soap derived from animal fiats. More recently, surfactants have been included in detergents to enhance their cleaning performance. Typical surfactants include anionics, nonionics, zwitterionics, ampholytics, cationics and those described in Surface Active Agents, Volumes I and II by Schwartz, Perry and Berch (New York, Interscience Publishers), Nonionic Surfactants, ed. by M. J. Schick (New York, M. Dekker, 1967), and in McCutcheon's Emulsifiers & Detergents (1989 Annual, M. C. Publishing Co.), the disclosures of which are incorporated herein by reference.

Anionic surfactants are a preferred type of surfactant for household care detergents due to their improved cleaning performance. The cleaning performance of anionic surfactants can be limited, however, by water hardness. Calcium and/or magnesium ions in hard water interfere with some anionic surfactants, such as alkyl olefin sulfonates, alkyl sulfates, linear alkyl sulfonates, and linear alkyl benzene sulfonates. Recently, interest in α-sulfofatty acid esters (also referred to hereafter as "sulfofatty acids") has increased due to the improved cleaning properties of these surfactants in hard water. While α-sulfofatty acid esters and other anionic surfactants have similar detergency in soft water, as water hardness increases α-sulfofatty acid esters exhibit better cleaning performance as compared with other anionic surfactants.

The use of α-sulfofatty acid esters has not been widely accepted, however, due to several disadvantages of such sulfofatty acids. In particular, α-sulfofatty acid esters tend to degrade to form di-salts during their manufacture. While mono-salts of α-sulfofatty acid esters have the desired surface active agent properties, di-salts have several undesirable properties that degrade the performance of the α-sulfofatty acid ester. For example, the Kraft point of a $C_{16}$ methyl ester sulfonate ("MES") di-salt is 65° C., as compared to 17° C. for the mono-salt form of $C_{16}$ MES. (The Kraft point is the temperature at which the solubility of an ionic surfactant becomes equal to its critical micelle concentration (CMC); below the Kraft point, surfactants form precipitates instead of micelles, and are far less effective at cleaning fabrics or in other household cleaning applications.) Thus, the higher the Kraft point, the more di-salt precipitates in the composition. The resulting poor di-salt solubility in cool and even slightly hard water is a disadvantage in most applications. Thus, significant amounts of di-salt in otherwise high quality α-sulfofatty acid ester degrade the performance of that sulfofatty acid. The presence of large amounts of di-salt in α-sulfofatty acid ester, therefore, results in a poorer quality α-sulfofatty acid ester product, characterized by degraded performance and reduced application flexibility.

Di-salts also result from hydrolysis of α-sulfofatty acid ester during storage and in detergent formulations. In particular, mono-salts of α-sulfofatty acid ester hydrolyze in the presence of moisture and alkali-containing detergent components to form di-salts. For example, in formulations where MES is well mixed with high pH components under aqueous conditions, the MES will hydrolyze nearly completely to the di-salt form. High pH components include builders, such as silicates or carbonates, and bases, such as sodium hydroxide (NaOH). This chemical instability discourages the use of α-sulfofatty acid esters in many applications.

A related problem associated with α-sulfofatty acid ester-containing detergent compositions is pH drift. In concentrated solutions, the pH of the solution drifts towards the acidic (lower) range. Such pH drift interferes with other detergent components in the composition. To prevent pH drift, buffering or alkalizing agents are added to detergents. Buffering or alkalizing agents, such as caustic soda (NaOH), cause additional di-salt formation, however, which decreases the performance of the α-sulfofatty acid ester.

α-Sulfofatty acid esters also have limited solubility in concentrated solutions, particularly when stored at lower temperatures. For example, phase separation occurs in concentrated solutions of $C_{16}$ or $C_{18}$ α-sulfofatty acid esters if the sulfofatty acid ester is not adequately solubilized. To prevent phase separation, a hydrotrope (a compound that is soluble in aqueous solutions and that increases the aqueous solubility of organic compounds) is often added to the detergent composition. Common hydrotropes include urea, lower molecular weight alkanols, glycols, and ammonium, potassium or sodium salts of toluene, xylene or cumene or ethyl benzene sulfonates. The latter hydrotropes tend to be more expensive, so less expensive hydrotropes, such as urea $((NH_2)_2CO)$ or urea-alkanol mixtures, are frequently used as cost-effective substitutes. Greater quantities of these hydrotropes are required, however, to achieve the stabilizing effects of the more expensive hydrotropes.

A disadvantage of urea-based hydrotropes, however, is that contaminants in urea release unpleasant odors. In particular, urea often contains ammonium carbamate $(NH_4CO_2NH_2)$, which hydrolyzes to release ammonia. If ammonia is released during washing, it can offend the consumer, leading to decreased consumer satisfaction with the product. Urea itself also slowly hydrolyzes to release ammonia. If high levels of urea are present, such hydrolysis tends to increase the pH of the composition. Such high pH values are generally incompatible with some uses of α-sulfofatty acid esters and with other detergent components.

Thus, there is a need for liquid compositions comprising surfactants or surfactant blends with high detergency, such as α-sulfofatty acid esters or blends thereof, and one or more additional components such as hydrotropes that solubilize the surfactant(s), such that the compositions remain as a more flowable liquid in cold temperatures, at high surfactant concentrations and/or in hard water conditions. Surprisingly, the present invention satisfies these needs.

SUMMARY OF THE INVENTION

The present invention provides compositions comprising at least one anionic surfactant, such as an α-sulfofatty acid ester, and at least one hydrotrope. According to the invention, effective amounts of α-sulfofatty acid ester and hydrotrope are combined to form a stabilized composition. In one such embodiment, the hydrotrope stabilizes the α-sulfofatty acid ester in solution and allows the composition to remain as a liquid in cold water. Particularly preferred are combinations of C16 methyl ester sulfonate (MES) and C18 MES, particularly eutectic MES which has a C16:C18 ratio of about 50:50 to about 70:30 (for example, about 50:50, about 55:45, about 60:40, about 65:35, about 70:30, about 75:25, or about 80:20). More particularly preferred are EMES with a C16:C18 ratio of about 70:30 and containing an alkyl amine oxide hydrotrope, e.g., a C6-C12 amine oxide hydrotrope, and particularly a C8 amine oxide hydrotrope, at amounts of about 1% to about 1% to about 10% (for example, at about 1%, about 2%, about 2.5%, about 2.75%, about 3%, about 3.5%, about 4%, about 4.5%, about 5%, about 5.5%, about 6%, about 6.5%, about 7%, about 7.5%, about 8%, about 8.5%, about 9%, about 9.5% or about 10%). EMES concentrations suitable for use in the present formulations include about 5% to about 50% (e.g., about 5%, about 6%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50%). Exemplary formulations include those described in the Examples herein, such as formulations containing about 35% EMES having a C16:C18 ratio of about 70:30 and containing a C8 amine oxide at levels of about 7%.

The present invention provides liquid detergent compositions which provide excellent solubility in cold water temperatures and also provide good overall cleaning performance, for example good stain-removal performance and whiteness maintenance performance in laundry applications. The liquid detergents form relatively transparent wash liquors upon contact with water and remain soluble in cold water temperatures in all household cleaning applications, including laundry cleaning, dishware cleaning, hard surface cleaning and personal care cleaning. The compositions of the present invention are particularly useful in cold water washing temperatures such as 40° C. or lower.

The compositions can optionally include detergent components. In one embodiment, suitable detergent components include, nonionic surfactants, other anionic surfactants, cationic surfactants, zwitterionic surfactants, polymer dispersants, builders, oxidizing agents, biocidal agents, foam regulators, activators, catalysts, thickeners, other stabilizers, fragrances, soil suspending agents, brighteners, enzymes, UV protectors, salts, water, inert ingredients, and the like. In another embodiment, the nonionic surfactant is a polyalkoxylated alkanolamide.

Suitable hydrotropes include amine oxides, benzene sulfonates, naphthalene sulfonates, short chain ($C_1$-$C_{12}$) alkyl benzene sulfonates, medium chain ($C_6$-$C_{12}$) alkyl sulfonates, medium chain ($C_6$-$C_{12}$) alkyl sulfates, alkylpolyglucosides, medium chain ($C_6$-$C_{12}$) alkyl dimethyl amine oxides, alkyl diphenyloxide disulfonates, and phosphate esters. Other suitable hydrotropes will be familiar to those of ordinary skill based on the disclosure herein and information readily available in the art.

Representative, non-limiting examples of medium chain ($C_6$-$C_{12}$) alkyl dimethyl amine oxides include, for example, hexyl dimethyl amine oxide, octyl dimethyl amine oxide, decyl dimethyl amine oxide, and lauryl dimethyl amine oxide. Particularly preferred are C6, C8, C10 and C12 dimethyl amine oxides, especially C6, C8 and C10 amine oxides such as hexyl dimethyl amine oxide, octyl dimethyl amine oxide, and decyl dimethyl amine oxide, respectively.

Methods of making compositions comprising α-sulfofatty acid ester and hydrotrope are also provided. Such methods generally include providing the α-sulfofatty acid ester and the hydrotrope, and mixing these components to form the composition. In another embodiment, detergent components are included in the composition. Such detergent components include, for example, nonionic surfactants, other anionic surfactants, cationic surfactants, zwitterionic surfactants, polymer dispersants, builders, oxidizing agents, biocidal agents, foam regulators, activators, catalysts, thickeners, other stabilizers, fragrances, soil suspending agents, brighteners, enzymes, UV protectors, salts, water, inert ingredients, and the like.

In additional embodiments, the invention also provides methods of use of the present compositions. One such embodiment provides a method of laundering a fabric comprising contacting a water solution comprising the fabric with a composition of the present invention. Another such embodiment provides a method of cleaning dishware comprising contacting the dishware with a water solution comprising a composition of the present invention. Still another such embodiment comprises a method of cleaning a household hard surface comprising contacting the hard surface with a water solution comprising a composition of the present invention. Still another such embodiment comprises a method of personal care cleaning comprising washing a part of a human body with a composition of the present invention. In each such embodiment, these methods of the invention can be performed at relatively low temperatures, for example under conditions wherein the water solution used in the methods is at a temperature of 50° F. or lower, 40° F. or lower, and the like.

Other embodiments suitably provided by the present invention will be familiar to one of ordinary skill in the art from the present description, drawings and claims.

BRIEF DESCRIPTION OF THE DRAWINGS

FIG. 6a: 25% (w/v) SunSoft™ EMES (defined as in the description of FIG. 5, above); FIG. 6b: 25% SunSolve™ EMES formulation, containing SunSoft™ and 2% C8 amine oxide; FIG. 6c: 35% SunSolve™ eutectic MES (EMES) formulation, containing SunSoft™ and 2% C8 amine oxide; FIG. 6d: 40% SunSolve™ EMES formulation, containing SunSoft™ and 7% C8 amine oxide.

DETAILED DESCRIPTION OF THE INVENTION

Figure 1:
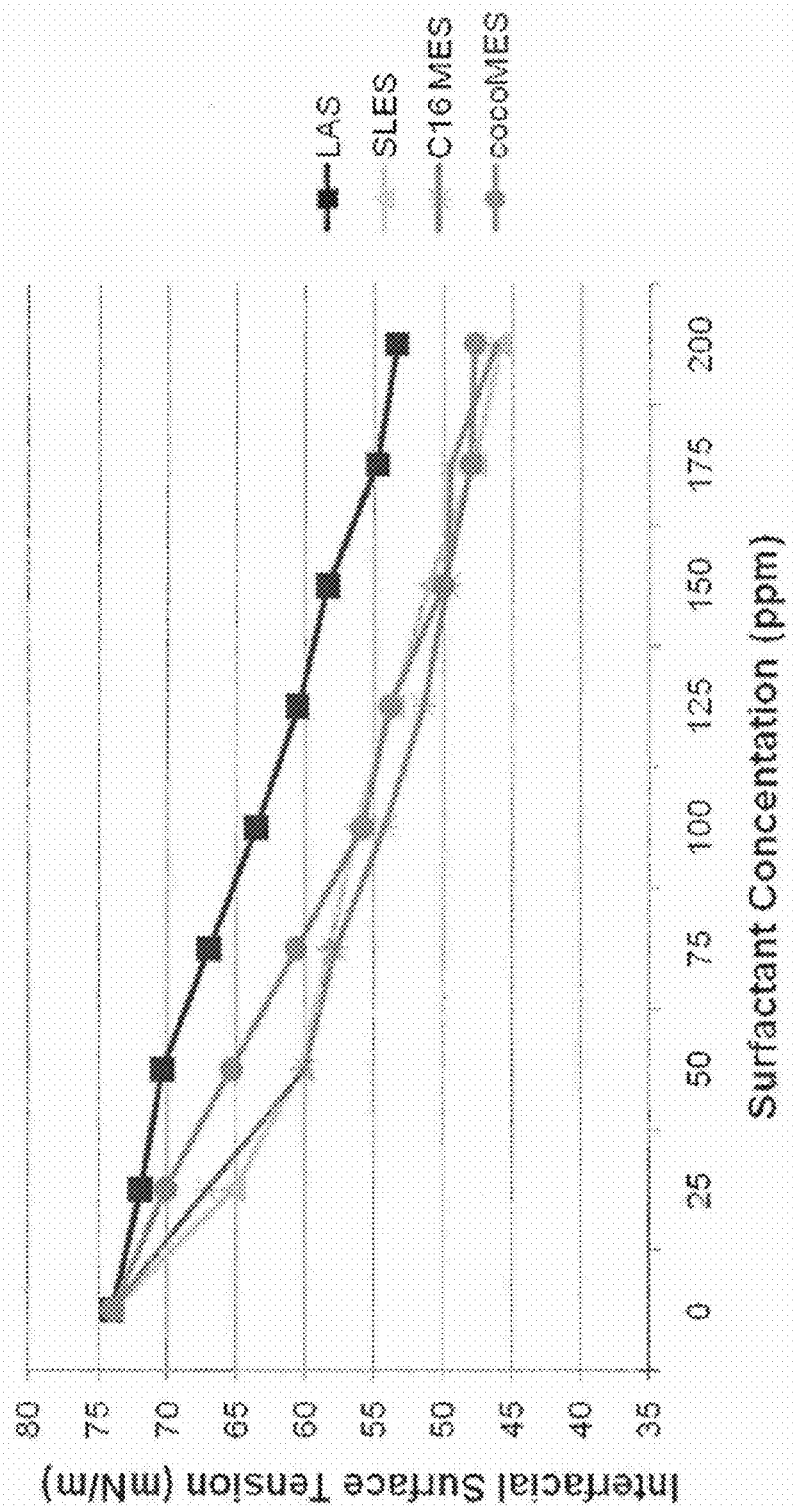
FIG. 1 is a line graph showing the interfacial surface tension of various anionic surfactants over increasing concentration. LAS: linear alkylbenzene sulfonate; SLES: sodium lauryl ether sulphate; C16 MES: methyl ester sulfonate (MES) having C16 alkyl fatty acid chains; cocoMES: MES having coco alkyl fatty acid chains.

The following description provides specific details, such as materials and dimensions, to provide a thorough understanding of the present invention. The skilled artisan, however, will appreciate that the present invention can be practiced without employing these specific details. Indeed, the present invention can be practiced in conjunction with processing, manufacturing or fabricating techniques conventionally used in the detergent industry. Moreover, the processes below describe only steps, rather than a complete process flow, for manufacturing the compositions and detergents containing the compositions according to the present invention.

The term "about" as used herein, includes the recited number±10%. Thus, "about ten" means 9 to 11.

One embodiment is directed to compositions comprising an α-sulfofatty acid ester and a hydrotrope. The α-sulfofatty acid ester and the hydrotrope are combined to form a stabilized composition according to the present invention.

The present invention is also directed to a composition comprising an α-sulfofatty acid ester and a hydrotrope that is disposed in a water soluble container.

The α-Sulfofatty Acid Ester

In a preferred embodiment, the composition comprises at least one α-sulfofatty acid ester. Such a sulfofatty acid is typically formed by esterifying a carboxylic acid with an alkanol and then sulfonating the α-position of the resulting ester. The α-sulfofatty acid ester is typically of the following formula (I):

wherein $R_1$ is a linear or branched alkane, $R_2$ is a linear or branched alkane, and $R_3$ is hydrogen, a halogen, a monovalent or di-valent cation, or an unsubstituted or substituted ammonium cation. $R_1$ can be a $C_4$ to $C_{24}$ alkane, including a $C_{10}$, $C_{12}$, $C_{14}$, $C_{16}$ and/or $C_{18}$ alkane. $R_2$ can be a $C_1$ to $C_8$ alkane, including a methyl group. $R_3$ is typically a monovalent or di-valent cation, such as a cation that forms a water soluble salt with the α-sulfofatty acid ester (e.g., an alkali metal salt such as sodium, potassium or lithium). The α-sulfofatty acid ester of formula (I) can be a methyl ester sulfonate, such as a $C_{16}$ methyl ester sulfonate, a $C_{18}$ methyl ester sulfonate, or a mixture thereof.

More typically, the α-sulfofatty acid ester is a salt, which is generally of the following formula (II):

wherein $R_1$ and $R_2$ are alkanes and M is a monovalent metal. For example, $R_1$ can be an alkane containing 4 to 24 carbon atoms, and is typically a $C_8$, $C_{10}$, $C_{12}$, $C_{14}$, $C_{16}$ and/or $C_{18}$ alkane. $R_2$ is typically an alkane containing 1 to 8 carbon atoms, and more typically a methyl group. M is typically an alkali metal, such as sodium or potassium. The α-sulfofatty acid ester of formula (II) can be a sodium methyl ester sulfonate, such as a sodium $C_8$-$C_{18}$ methyl ester sulfonate.

In one embodiment, the composition comprises at least one α-sulfofatty acid ester. For example, the α-sulfofatty acid ester can be a $C_{10}$, $C_{12}$, $C_{14}$, $C_{16}$ or $C_{18}$ α-sulfofatty acid ester. In another embodiment, the α-sulfofatty acid ester comprises a mixture of sulfofatty acids. For example, the composition can comprise a mixture of α-sulfofatty acid esters, such as $C_{10}$, $C_{12}$, $C_{14}$, $C_{16}$ and $C_{18}$ sulfofatty acids. The proportions of different chain lengths in the mixture are selected according to the properties of the α-sulfofatty acid esters. For example, $C_{16}$ and $C_{18}$ sulfofatty acids (e.g., from tallow and/or palm stearin MES) generally provide better surface active agent properties, but are less soluble in aqueous solutions. $C_{10}$, $C_{12}$ and $C_{14}$ α-sulfofatty acid esters (e.g., from palm kernel oil or coconut oil) are more soluble in water, but have lesser surface active agent properties. Suitable mixtures include $C_8$, $C_{10}$, $C_{12}$ and/or $C_{14}$ α-sulfofatty acid esters with $C_{16}$ and/or $C_{18}$ α-sulfofatty acid esters. For example, about 1 to about 99 percent of $C_8$, $C_{10}$, $C_{12}$ and/or $C_{14}$ α-sulfofatty acid ester can be combined with about 99 to about 1 weight percent of $C_{16}$ and/or $C_{18}$ α-sulfofatty acid ester. In another embodiment, the mixture comprises about 1 to about 99 weight percent of a $C_{16}$ or $C_{18}$ α-sulfofatty acid ester and about 99 to about 1 weight percent of a $C_{16}$ or $C_{18}$ α-sulfofatty acid ester. In yet another embodiment, the α-sulfofatty acid ester is a mixture of $C_{18}$ methyl ester sulfonate and a $C_{16}$ methyl ester sulfonate and having a ratio of about 2:1 to about 1:3. Particularly preferred are combinations of $C_{16}$ methyl ester sulfonate (MES) and $C_{18}$ MES, particularly eutectic MES (referred to herein as EMES) which has a C16:C18 ratio of about 50:50 to about 70:30 (for example, about 50:50, about 55:45, about 60:40, about 65:35, about 70:30, about 75:25, or about 80:20, and most particularly a C16:C18 ratio of about 70:30).

The composition can also be enriched for certain α-sulfofatty acid esters, as disclosed in co-pending U.S. Pat. No. 6,683,039, to provide the desired surfactant properties. The disclosure of that application is incorporated by reference herein. For example, α-sulfofatty acid esters prepared from natural sources, such as palm kernel (stearin) oil, palm kernel (olein) oil, or beef tallow, are enriched for $C_{16}$ and/or $C_{18}$ α-sulfofatty acid esters by addition of the purified or semi-purified α-sulfofatty acid esters to a mixture of α-sulfofatty acid esters. Suitable ratios for enrichment range from greater than 0.5:1, about 1:1, about 1.5:1, to greater than 2:1, and up to about 5 to about 6:1, or more, of $C_{16}$-$C_{18}$ to other chain length α-sulfofatty acid esters. An enriched mixture can also comprise about 50 to about 60 weight percent $C_8$-$C_{18}$ α-sulfofatty acid esters and about 40 to about 50 weight percent $C_{16}$ α-sulfofatty acid ester.

Methods of preparing α-sulfofatty acid esters are known to the skilled artisan. (See, e.g., U.S. Pat. Nos. 5,587,500; 5,384,422; 5,382,677; 5,329,030; 4,816,188; and 4,671,900; the disclosures of which are incorporated herein by reference.) α-Sulfofatty acid esters can be prepared from a variety of sources, including beef tallow, palm kernel oil, palm kernel (olein) oil, palm kernel (stearin) oil, coconut oil, soybean oil, canola oil, cohune oil, coco butter, palm oil, white grease, cottonseed oil, corn oil, rape seed oil, soybean oil, yellow grease, mixtures thereof or fractions thereof. Other sources of fatty acids to make α-sulfofatty acid esters include caprylic ($C_8$), capric ($C_{10}$), lauric ($C_{12}$), myristic ($C_{14}$), myristoleic ($C_{14}$), palmitic ($C_{16}$), palmitoleic ($C_{16}$), stearic ($C_{18}$), oleic ($C_{18}$), linoleic ($C_{18}$), linolenic ($C_{18}$), ricinoleic ($C_{18}$), arachidic ($C_{20}$), gadolic ($C_{20}$), behenic ($C_{22}$) and erucic ($C_{22}$) fatty acids. α-Sulfofatty acid esters prepared from one or more of these sources are within the scope of the present invention.

The compositions according to the present invention comprise an effective amount of α-sulfofatty acid ester (i.e., an amount which exhibits the desired cleaning and surfactant properties). In one embodiment, an effective amount is at least about 0.5 weight percent α-sulfofatty acid ester. In another embodiment, the effective amount is at least about 1 weight percent α-sulfofatty acid ester. In another embodiment, an effective amount is at least about 5 weight percent α-sulfofatty acid ester. In still another embodiment, an effective amount of the α-sulfofatty acid ester is at least about 10 weight percent, at least about 25 weight percent, or at least about 30 weight percent. In another embodiment, an effective amount is from 0.5 weight percent to 30 weight percent α-sulfofatty acid ester, preferably from 0.5 weight percent to 25 weight percent, or from 1 weight percent to 25 weight percent, or from 1 weight percent to 10 weight percent, or from 5 weight percent to 10 weight percent. These weight percentages are based on the total weight of the composition. Suitable compositions containing EMES according to the present invention include, for example, EMES concentrations at about 5% to about 50% (e.g., about 5%, about 6%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45% or about 50%). Exemplary formulations include those described in the Examples herein, such as formulations containing about 25%, 30% or 35%.

Hydrotrope

The compositions are stabilized (i.e., the solubility of the surfactant at cold temperatures and upon long-term storage is maintained) by including an effective amount of at least one hydrotrope. The hydrotrope provides one or more stabilizing effects to the α-sulfofatty acid ester-containing containing composition. In one embodiment, the hydrotrope aids in a solubilizing the α-sulfofatty acid ester in a cold water aqueous solution. In another embodiment, the hydrotrope aids in solubilizing the α-sulfofatty acid ester in a cold water aqueous solution wherein the temperature is less than 40° C. In such embodiments, the hydrotrope provides such stabilizing effects to the composition either in cold temperature storage conditions, in use in cold water laundry conditions, or both.

In another embodiment, effective amounts of the α-sulfofatty acid ester and the hydrotrope stabilize the composition by reducing pH drift towards either more acidic or more basic values. The α-sulfofatty acid ester(s) is combined with an effective amount of the hydrotrope to stabilize the pH of the composition within a desired range, as compared with a non-stabilized composition. In another embodiment, the effective amount of hydrotrope reduces pH drift outside the desired pH range during storage. The effective amount of the hydrotrope is determined, for example, according to the intended shelf life of the composition, so that the pH of the composition remains within the desired pH range during to storage.

In another embodiment, the hydrotrope is compatible with the α-sulfofatty acid ester, so that no more than a minor amount of additional di-salt forms in the composition. The hydrotrope can stabilize the composition by reducing pH drift, thereby sparing the requirement for alkalizing agents. As used herein, the term a "minor amount" means no more than about 30 weight percent additional di-salt. More typically, a minor amount is no more than about 15 weight percent additional di-salt, or no more than about 7 weight percent additional di-salt. As will be appreciated by the skilled artisan, the preceding ranges apply to additional di-salt formation and exclude di-salt already present in the α-sulfofatty acid ester as a result of the manufacturing process. The method of George Battaglini et al., "Analytical Methods for Alpha Sulfo Methyl Tallowate," *JOACS* 63: 8 (August, 1986), can be used to determine the amount of di-salt in an α-sulfofatty acid ester sample, and any increase in such a sample as compared with a control sample. The disclosure of this publication is incorporated by reference herein.

In one embodiment, the hydrotrope is a medium chain ($C_4$-$C_{18}$) alkyl dimethyl amine oxide such as octyl dimethyl amine oxide, decyl dimethyl amine oxide, lauryl dimethyl amine oxide, and myristyl dimethyl amine oxide. In another embodiment, the hydrotrope is a medium chain ($C_4$-$C_{18}$) alkyl dimethyl amine oxide that comprises a mixture of alkyl dimethyl amine oxides. For example, the composition can comprise a mixture of alkyl dimethyl amine oxides, such as $C_4$, $C_6$, $C_8$, $C_{10}$, $C_{12}$, $C_{14}$, $C_{16}$ and $C_{18}$ alkyl dimethyl amine oxides. The proportions of different chain lengths in the mixture are selected according to the properties of the alkyl dimethyl amine oxides. Particularly useful in this aspect of the invention are $C_6$, $C_8$ and $C_{10}$, alkyl dimethyl amine oxides, and more particularly $C_8$ alkyl dimethyl amine oxides. Amine oxides used according to this aspect of the invention can be either synthetic or natural, and are available commercially from a variety of suppliers, including Stepan Company (e.g., Stepan Agent 3785-87 or synthetic C8 3853-01), Lonza (e.g., Lonza FMB AO-8), Clariant (e.g., GEMAMINOX®. OC), Mason (e.g., MACAT® AO-8), Rhodia (e.g., MACKAMINE® C8), and The Sun Products Corporation.

In one embodiment, the α-sulfofatty acid ester is combined with an effective amount of hydrotrope to aid in solubilizing the α-sulfofatty acid ester in cold water solution. In one embodiment, an effective amount is at least about 0.5 weight percent hydrotrope. In another embodiment, the effective amount is at least about 1 weight percent hydrotrope. In another embodiment, an effective amount is at least about 5 weight percent hydrotrope. In still another embodiment, an effective amount of hydrotrope is at least about 10 weight percent, at least about 25 weight percent, or at least about 30 weight percent. In another embodiment, an effective amount is from 0.5 weight percent to 30 weight percent hydrotrope, preferably from 0.5 weight percent to 25 weight percent, or from 0.5 weight percent to 10 weight percent, or from 1 weight percent to 25 weight percent, or from 1 weight percent to 10 weight percent, or from 1 weight percent to 5 weight percent, or from 1.5 weight percent to about 3 weight percent, or from 2 weight percent to about 2.5 weight percent, or from 5 weight percent to 10 weight percent, or from about 2.5 weight percent to about 5 weight percent, or from about 2 weight percent to about 4 weight percent, or about 5 weight percent. In additional embodiments, a C8 amine oxide hydrotrope is included in the MES- (e.g., EMES-) containing formulations of the invention at amounts of about 1% to about 10% (for example, at about 1%, about 2%, about 2.5%, about 2.75%, about 3%, about 3.5%, about 4%, about 4.5%, about 5%, about 5.5%, about 6%, about 6.5%, about 7%, about 7.5%, about 8%, about 8.5%, about 9%, about 9.5% or about 10%). Exemplary formulations include those described in the Examples herein, such as formulations containing about 35% EMES having a C16:C18 ratio of about 70:30 and containing a C8 amine oxide at levels of about 7%. These weight percentages are based on the total weight of the composition.

The compositions can optionally further include a secondary hydrotrope. Such a secondary hydrotrope can be a Kraft point reducer that helps prevent precipitation of the α-sulfofatty acid ester at lower temperatures. As will be appreciated by the skilled artisan, precipitation is generally indicated by the presence of white turbidity in the solution. examples of suitable Kraft point reducers include, but are not limited to, pyrrolidones, such as, for example, N-octyl pyrrolidone (SURFADONE®, International Specialty Products, UK), the pyridone salts disclosed in U.S. Pat. No. 4,367,169, the disclosure of which is incorporated by reference herein, and the like. In one embodiment, the composition comprises about 1% to about 5% (e.g., about 2%) by weight of the Kraft point reducer, although greater and lesser amounts can be used. Examples of suitable such secondary hydrotropes are described elsewhere herein, including in the Examples, and will be familiar to those of ordinary skill in the art, and include compounds such as triethanolamine, betaines, alkylglucosides, polyalkylglucosides, glycerine, certain short-chain organic alcohols (e.g., ethanol), propylene glycol and even longer-alkyl chain (e.g., $C_{10}$-$C_{14}$) amine oxides.

Other Components

In additional embodiments, the compositions of the invention may comprise one or more additional components. For example, for producing certain compositions in which flowability of the liquid composition is important (e.g., for detergent, dish or personal care compositions in which it may be desirable to package the composition in a hand pump-containing dispenser), it is desirable to include in the composition one or more viscosity-modifying agents, such as a solvent like an organic alcohol (e.g., ethanol). Exemplary such compositions will comprise from about 3% to about 10%, preferably from about 5% to about 8%, of the solvent. It should be noted, however, that the use of such a solvent is not absolutely required, as most of the formulations described herein (particularly those having MES surfactant levels at about 30% to about 40% and C8 amine oxide hydrotrope levels at about 2% to about 7%) are pumpable in conditions where the formulations undergo high shear stress via the pumping action (whereby the viscosity is reduced). Suitable such formulations are described in the Examples herein.

In additional preferred embodiments, the compositions include one or more other components, such as nonionic surfactants, other (secondary) anionic surfactants, cationic surfactants, zwitterionic surfactants, polymer dispersants, builders, oxidizing agents, biocidal agents, foam regulators, activators, catalysts, thickeners, other stabilizers, fragrances, soil suspending agents, brighteners, enzymes, UV protectors, salts, water, inert ingredients, and the like.

Suitable nonionic surfactants include polyalkoxylated alkanolamides, which are generally of the following formula (II):

(III)

wherein $R_4$ is an alkane or hydroalkane, $R_5$ and $R_7$ are alkanes and n is a positive integer. $R_4$ is typically an alkane containing 6 to 22 carbon atoms. $R_5$ is typically an alkane containing 1-8 carbon atoms. $R_7$ is typically an alkane containing 1 to 4 carbon atoms, and more typically an ethyl group. The degree of polyalkoxylation (the molar ratio of the oxyalkyl groups per mole of alkanolamide) typically ranges from about 1 to about 100, or from about 3 to about 8, or about 5 to about 6. $R_6$ can be hydrogen, an alkane, a hydroalkane group or a polyalkoxylated alkane. The polyalkoxylated alkanolamide is typically a polyalkoxylated mono- or di-alkanolamide, such as a $C_{16}$ and/or $C_{18}$ ethoxylated monoalkanolamide, or an ethoxylated monoalkanolamide prepared from palm kernel oil or coconut oil.

Methods of manufacturing polyalkoxylated alkanolamides are known to the skilled artisan. (See, e.g., U.S. Pat. Nos. 6,034,257 and 6,034,257, the disclosure of which are incorporated by reference herein.) Sources of fatty acids for the preparation of alkanolamides include beef tallow, palm kernel (stearin or olein) oil, coconut oil, soybean oil, canola oil, cohune oil, palm oil, white grease, cottonseed oil, mixtures thereof and fractions thereof. Other sources include caprylic ($C_8$), capric ($C_{10}$), lauric ($C_{12}$), myristic ($C_{14}$), myristoleic ($C_{14}$), palmitic ($C_{16}$), palmitoleic ($C_{16}$), stearic ($C_{18}$), oleic ($C_{18}$), linoleic ($C_{18}$), linolenic ($C_{18}$), ricinoleic ($C_{18}$), arachidic ($C_{20}$), gadolic ($C_{20}$), behenic ($C_{22}$) and erucic ($C_{22}$) fatty acids. Polyalkoxylated alkanolamides from one or more of these sources are within the scope of the present invention.

The composition typically comprises an effective amount of polyalkoxylated alkanolamide (e.g., an amount which exhibits the desired surfactant properties). In some applications, the composition contains about 1 to about 10 weight percent of a polyalkoxylated alkanolamide. Typically, the composition comprises at least about one weight percent of polyalkoxylated alkanolamide.

Other suitable nonionic surfactants include those containing an organic hydrophobic group and a hydrophilic group that is a reaction product of a solubilizing group (such as a carboxylate, hydroxyl, amido or amino group) with an alkylating agent, such as ethylene oxide, propylene oxide, or a polyhydration product thereof (such as polyethylene glycol). Such nonionic surfactants include, for example, polyoxyalkylene alkyl ethers, polyoxyalkylene alkylphenyl ethers, polyoxyalkylene sorbitan fatty acid esters, polyoxyalkylene sorbitol fatty acid esters, polyalkylene glycol fatty acid esters, alkyl polyalkylene glycol fatty acid esters, polyoxyethylene polyoxypropylene alkyl ethers, polyoxyalkylene castor oils, polyoxyalkylene alkylamines, glycerol fatty acid esters, alkylglucosamides, alkylglucosides, and alkylamine oxides. Other suitable surfactants include those disclosed in U.S. Pat. Nos. 5,945,394 and 6,046,149, the disclosures of which are incorporated herein by reference. In another embodiment, the composition is substantially free of nonylphenol nonionic surfactants. In this context, the term "substantially free" means less than about one weight percent.

Polymer dispersants, such as polymers and co-polymers of acrylic acid, methacrylic acid, maleic acid, fumaric acid, itaconic acid, and water-soluble salts thereof, such as alkali metal, ammonium, or substituted ammonium salts, can optionally be included in the composition. Suitable polymer dispersants further include those sold under the trade names ACUSOL® 445 (polyacrylic acid), ACUSOL® 445N (polyacrylic acid sodium salt), ACUSOL® 460N (a maleic acid/olefin copolymer sodium salt), and ACUSOL® 820 (acrylic copolymer), sold by Rohm and Haas Company.

In an embodiment, a secondary anionic surfactant is included in the composition. Suitable secondary anionic surfactants includes those surfactants that contain a long chain hydrocarbon hydrophobic group in their molecular structure and a hydrophilic group, i.e., water solubilizing group including salts such as carboxylate, sulfonate, sulfate or phosphate groups. Suitable anionic surfactant salts include sodium, potassium, calcium, magnesium, barium, iron, ammonium and amine salts. Other suitable secondary anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water soluble salts of alkyl benzene sulfonates having between 8 and 22 carbon atoms in the alkyl group, alkyl ether sulfates having between 8 and 22 carbon atoms in the alkyl group. Other anionic surfactants include polyethoxylated alcohol sulfates, such as those sold under the trade name CALFOAM® 303 (Pilot Chemical Company, California). Examples of other anionic surfactants are disclosed in U.S. Pat. No. 3,976,586, the disclosure of which is incorporated by reference herein. In another embodiment, the composition is substantially free of additional (secondary) anionic surfactants.

Suitable zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds, such as those disclosed in U.S. Pat. No. 3,929,678, which is incorporated by reference herein.

Other suitable components include organic or inorganic detergency builders. Examples of water-soluble inorganic builders that can be used, either alone or in combination with themselves or with organic alkaline sequestrant builder salts, are glycine, alkyl and alkenyl succinates, alkali metal carbonates, alkali metal bicarbonates, phosphates, polyphosphates and silicates. Specific examples of such salts are sodium tripolyphosphate, sodium carbonate, potassium carbonate, sodium bicarbonate, potassium bicarbonate, sodium pyrophosphate and potassium pyrophosphate. Examples of organic builder salts that can be used alone, or in combination with each other, or with the preceding inorganic alkaline builder salts, are alkali metal polycarboxylates, water-soluble citrates such as sodium and potassium citrate, sodium and potassium tartrate, sodium and potassium ethylenediaminetetraacetate, sodium and potassium N(2-hydroxyethyl)-nitrilo triacetates, sodium and potassium N-(2-hydroxyethyl)-nitrilo diacetates, sodium and potassium oxydisuccinates, and sodium and potassium tartrate mono- and di-succinates, such as those described in U.S. Pat. No. 4,663,071, the disclosure of which is incorporated herein by reference.

Suitable biocidal agents include triclosan (5-chloro-2 (2,4-dichloro-phenoxy)phenol)), and the like. Suitable optical brighteners include stilbenes such as TINOPAL® AMS, distyrylbiphenyl derivatives such as TINOPAL® CBS-X, stilbene/naphthotriazole blends such as TINOPAL® RA-16, all sold by Ciba Geigy, oxazole derivatives, and coumarin brighteners.

Suitable enzymes include those known in the art, such as amylolytic, proteolytic, cellulolytic or lipolytic type, and those listed in U.S. Pat. No. 5,958,864, the disclosure of which is incorporated herein by reference. One preferred protease, sold under the trade name SAVINASE® by Novozymes A/S, is a subtilase from Bacillus lentus. Other suitable enzymes include proteases, amylases, lipases and cellulases, such as ALCALASE® (bacterial protease), EVERLASE® (protein-engineered variant of SAVINASE®), ESPERASE® (bacterial protease), LIPOLASE® (fungal lipase), LIPOLASE ULTRA (Protein-engineered variant of LIPOLASE), LIPOPRIME® (protein-engineered variant of LIPOLASE), TERMAMYL® (bacterial amylase), BAN (Bacterial Amylase Novo), CELLUZYME® (fungal enzyme), and CAREZYME® (monocomponent cellulase), sold by Novozymes A/S. Additional enzymes of these classes suitable for use in accordance with the present invention will be well-known to those of ordinary skill in the art, and are available from a variety of commercial suppliers including but not limited to Novozymes A/S and Genencor/Danisco.

Suitable foam stabilizing agents include a polyalkoxylated alkanolamide, amide, amine oxide, betaine, sultaine, $C_8$-$C_{18}$ fatty alcohols, and those disclosed in U.S. Pat. No. 5,616,781, the disclosure of which is incorporated by reference herein. Foam stabilizing agents are used, for example, in amounts of about 1 to about 20, typically about 3 to about 5 percent by weight. The composition can further include an auxiliary foam stabilizing surfactant, such as a fatty acid amide surfactant. Suitable fatty acid amides are $C_8$-$C_{20}$ alkanol amides, monoethanolamides, diethanolamides, and isopropanolamides.

Suitable liquid carriers include water, a mixture of water and a $C_1$-$C_4$ monohydric alcohol (e.g., ethanol, propanol, isopropanol, butanol, and mixtures thereof), and the like. In one embodiment, a liquid carrier comprises from about 90% to about 25% by weight, typically about 80% to about 50% by weight, more typically about 70% to about 60% by weight of the composition. Other suitable components include diluents, dyes and perfumes. Diluents can be inorganic salts, such as sodium and potassium sulfate, ammonium chloride, sodium and potassium chloride, sodium bicarbonate, and the like. Such diluents are typically present at levels of from about 1% to about 10%, preferably from about 2% to about 5% by weight.

In some embodiments, the compositions of the present invention may be contained in a container, which in certain such embodiments is a water-soluble container. In such embodiments, the water soluble container is made from a water-soluble material which dissolves, ruptures, disperses, or disintegrates upon contact with water, releasing thereby the composition. In some embodiments, the water soluble container is formed from a water soluble polymer selected from the group consisting of polyvinyl alcohol, cellulose ethers, polyethylene oxide, starch, polyvinylpyrrolidone, polyacrylamide, polyacrylonitrile, polyvinyl methyl ether-maleic anhydride, polymaleic anhydride, styrene maleic anhydride, hydroxyethylcellulose, methylcellulose, polyethylene glycols, carboxymethylcellulose, polyacrylic acid salts, alginates, acrylamide copolymers, guar gum, casein, ethylene-maleic anhydride resins, polyethyleneimine, ethyl hydroxyethylcellulose, ethyl methylcellulose, hydroxyethyl methylcellulose, and mixtures thereof. In one embodiment, the water soluble container is made from a lower molecular weight water-soluble polyvinyl alcohol film-forming resin.

Unit dose containers and methods of manufacture thereof that are suitable for use with the compositions of the present invention include those described, for example, in U.S. Pat. Nos. 3,218,776; 4,776,455; 6,727,215; 6,878,679; 7,259,134; 7,282,472; 7,304,025; 7,329,441; 7,439,215; 7,464,519; and 7,595,290; and in U.S. Published Application No. 2012/0108487 A1; the disclosures of all of which are incorporated herein by reference in their entireties. In preferred such embodiments, the container is a water-soluble, single-chamber container, prepared from a water-soluble film. According to one such aspect of the invention, the single-chamber container is a formed, sealed pouch produced from a water-soluble polymer or film such as polyvinylalcohol (PVOH) or a PVOH film.

Preferred water soluble polymers for forming the pouch are polyvinyl alcohol (PVOH) resins sold under tradename MONOSOL® (MonoSol LLC, Indiana). The preferred grade is MONOSOL® film having a weight average molecular weight range of about 55,000 to 65,000 and a number average molecular weight range of about 27,000 to 33,000. Preferably, the film material will have a thickness of approximately 3 mil or 75 micrometers. Alternatively, commercial grade PVOH films are suitable for use in the present invention, such as those that are commercially available from Monosol (Merrillville, Ind.) (e.g., Monosol film M8630) or from Aicello (Aiichi, Japan; North American subsidiary in North Vancouver, BC, Canada) (e.g., Aicello fill PT75).

In some embodiments, the water soluble container further comprises a cross-linking agent. In some embodiments, the cross-linking agent is selected from the group consisting of formaldehyde, polyesters, epoxides, isocyanates, vinyl esters, urethanes, polyimides, acrylics with hydroxyl, carboxylic, isocyanate or activated ester groups, bis(methacryloxypropyl)tetramethylsiloxane (styrenes, methylmetacrylates), n-diazopyruvates, phenylboronic acids, cis-platin, divinylbenzene (styrenes, double bonds), polyamides, dialdehydes, triallyl cyanurates, N-(2-ethanesulfonylethyl)pyridinium halides, tetraalkyltitanates, titanates, borates, zirconates, or mixtures thereof. In one embodiment, the cross-linking agent is boric acid or sodium borate.

In additional embodiments, the water-soluble container or film from which it is made can contain one or more additional components, agents or features, such as one or more perfumes or fragrances, one or more enzymes, one or more surfactants, one or more rinse agents, one or more dyes, one or more functional or aesthetic particles, and the like. Such components, agents or features can be incorporate into or on the film when it is manufactured, or are conveniently introduced onto the film during the process of manufacturing the cleaning compositions of the present invention, using methods that are known in the film-producing arts.

The single-compartment, water-soluble container (e.g., pouch) used in association with the present compositions may be in any desirable shape and size and may be prepared in any suitable way, such as via molding, casting, extruding or blowing, and is then filled using an automated filling process. Examples of processes for producing and filling water-soluble containers, suitable for use in accordance with the present invention, are described in U.S. Pat. Nos. 3,218,776; 3,453,779; 4,776,455; 5,699,653; 5,722,217; 6,037,319; 6,727,215; 6,878,679; 7,259,134; 7,282,472; 7,304,025; 7,329,441; 7,439,215; 7,464,519; and 7,595,290; the disclosures of all of which are incorporated herein by reference in their entireties. In preferred embodiments, the pouches are filled with the STTC and/or the cleaning agent composition of the present invention using the cavity filling approach described in U.S. Pat. Nos. 3,218,776 and 4,776,455; machinery necessary for carrying out this process is commercially available, e.g., from Cloud Packaging Solutions (Des Plaines, Ill.; a division of Ryt-way industries, LLC, Lakeville, Minn.).

In some embodiments, the water soluble container comprises a protective layer between the film polymer and the composition in the pouch. In some embodiments, the protective layer comprises polytetrafluoroethylene (PTFE).

In one embodiment, the liquid composition can be put in unit dose sachets, which can be water-soluble or water-permeable, to release the product when added to water.

Compositions according to the present invention are formed by any suitable method known to the skilled artisan. Typically, effective amounts of α-sulfofatty acid ester and hydrotrope are combined to form the composition. In one embodiment, the hydrotrope (e.g., the alkyl dimethyl amine oxide) is solubilized in a liquid carrier (e.g., water) prior to addition to the α-sulfofatty acid ester, which may be in the form of an aqueous solution. In a related embodiment, the hydrotrope (e.g., the alkyl dimethyl amine oxide) is solubilized in a liquid carrier (e.g., water) and mixed with the α-sulfofatty acid ester, which may be in the form of an aqueous solution, to form a blend, and then this blend added to a formulation (e.g., an aqueous composition) comprising one or more other laundry detergent components such as those described herein. Other suitable methods include those described in Perry's Chemical Engineers' Handbook (6th Ed.), chapter 19 (1984), the disclosure of which is incorporated by reference herein. In another embodiment, effective amounts of α-sulfofatty acid ester, the hydrotrope, and other detergent components are combined, according to the desired properties of, or their desired individual proportions in, the final composition. For example, the α-sulfofatty acid ester and hydrotrope are combined in a mixer, other detergent components are added, then the components are mixed to form a composition, according to the present invention.

Other embodiments of the present invention are exemplified in the following examples, which illustrate embodiments according to the present invention, although the invention is not intended to be limited by or to these examples.

EXAMPLES

Example 1

Analyses of Surfactant Solubility

Methyl ester sulfonate (MES) is an efficient, cost effective surfactant with broad application in soaps and detergents. It is commonly used in a number of household cleaning products, including laundry (powders and liquids) and manual dishwash detergents, is derived from renewable resources and is biodegradable. MES is also cost-competitive with traditional surfactants used in these applications, including linear alkylbenzene sulfonate (LAS), and has a number of additional advantages over LAS including its hard water tolerance (reducing the need for builders in MES-containing formulations), its low odor profile (reducing the amount of fragrance needed to overcome the base odor), its gentleness on skin (making it particularly useful in laundry and hand dish applications where skin contact is common), and the fact that little waste is created in the production of MES compared to LAS. Finally, in compacted powder products, MES can be post-added via powder blending, which enables better control of the bulk density of the finished compacted powder formulation.

Despite these apparent advantages, however, MES has traditionally found limited use or acceptance in detergent formulations, for several reasons. First, many grades of MES are "deficient" in detergency, and those that show suitable detergency often have limited solubility in water. Moreover, the solubility even of those MES components that show suitable detergency is even further reduced in formulations that are stored or used at low temperatures (e.g., below about 50° F.) as is commonly used in so-called "cold water" laundry applications. In addition, there are pH constraints on the formulations in which MES is to be used; if pH of the formulation is not tightly controlled, disalt formation occurs which drastically reduces the solubility and detergency of the MES even further. It can also often be difficult to control the color profile of MES in powder formulations, which can lead to the production of formulations that do not show long-term storage stability, reducing the commercial suitability of the formulations. Finally, the use of MES often requires sophisticated equipment and technical expertise to deliver consistently high quality material. In the present invention, we have addressed many of these potential downsides to using MES, to determine the optimum form of MES, and formulation(s) containing MES, suitable for use in detergent applications such as laundry and dish cleaning.

First, we addressed the fact that MES has typically been thought of as a component that can show poor detergency. A surfactant's cleaning performance (i.e., detergency) can be measured directly by an examination of its interfacial tension (IFT) as a function of its critical micelle concentration (CMC, the concentration where the surfactant's monomers arrange themselves in a spherical shape so that their hydrophobic tails can trap oil). We therefore wanted to examine the suitability of various surfactants, including various types of MES, for use in reducing surface tension (i.e., detergency) over various surfactant concentrations. Surfactants were titrated in water at concentrations from 0 to 250 ppm (which is typical of "in use" conditions for surfactant formulations in household laundry methods), and the interfacial surface tension of these solutions was measured as a function of concentration using the pendant drop method on a Kruss DSA100 drop shape analyzer. This method allows for rapid, accurate determination of surface tension through analysis of drop shape, by Computational fit to the Young-Laplace equation:

$$\Delta p = \gamma(1/R_x + 1/R_y),$$

where $\Delta p$ is the pressure difference across the fluid interface, $\gamma$ is the surface tension, and $R_x$ and $R_y$ are the principal radii of curvature of the drop. As one of ordinary skill will readily understand, other tensiometric methods of determining interfacial surface tension can also be used, for example using a Du Nouy ring, drop volume, or bubble tensiometer; suitable instrumentation and methods for measuring surface tension using such approaches are well-known in the art. Such approaches are also suitable for determining CMC of various compositions; in the present studies, CMC was also determined using the Krus DSA100 instrument. Results are shown in FIG. 1.

The results showed that among several well-known surfactants that are commonly used in household cleaning products, MES (whether in C16 form or coco form) reaches its CMC the quickest and also exhibits the lowest IFT at each concentration measured. These results demonstrate that amongst these surfactants, MES demonstrates enhanced wetting or detergency (i.e., a more rapidly developing reduction in surface tension) at a relatively low CMC, making it a suitable surfactant candidate.

Figure 2:
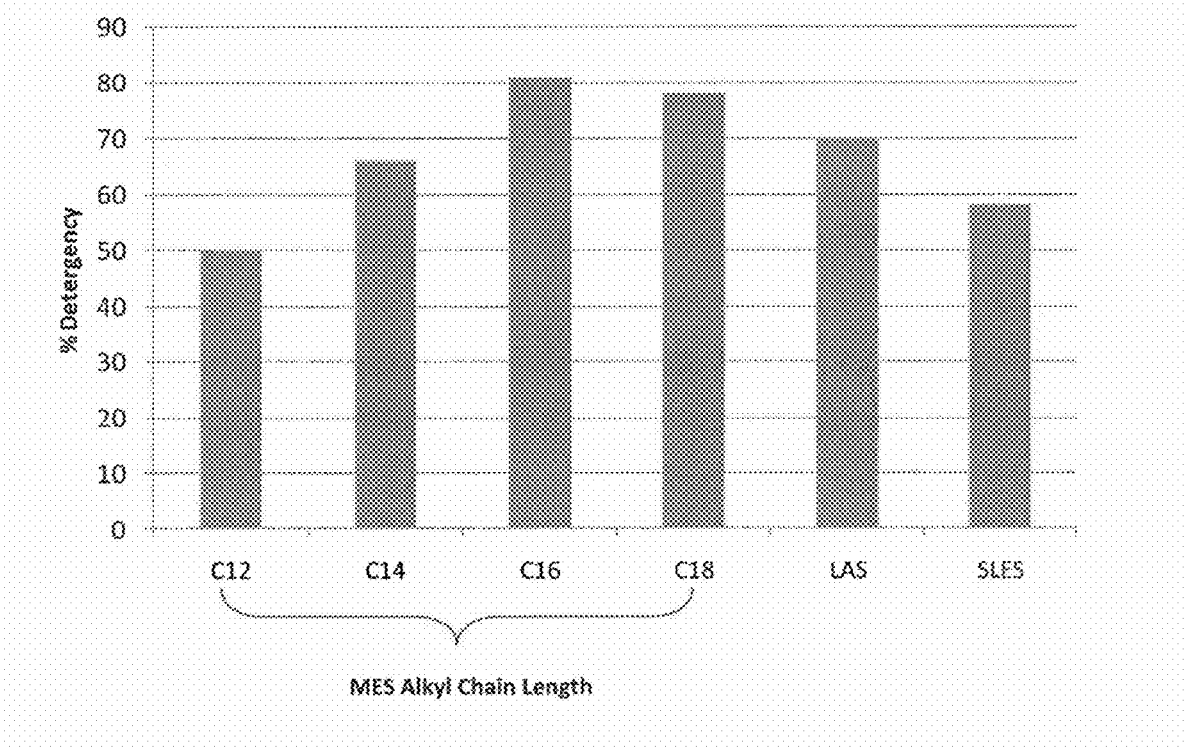
FIG. 2 is a bar graph showing the percent detergency of various surfactants. C12-C18 are MESs having the indicated alkyl chain length; LAS and SLES are as defined in the description of FIG. 1 above.

Importantly, we have also found that chain length of the MES sulfofatty acid chains impacted detergency as well. Specifically, it was found that with longer chain lengths, detergency improved. The IFT studies described above were repeated using MES having an alkyl chain length varying from twelve carbons ($C_{12}$) to 18 carbons ($C_{18}$). Results are shown in FIG. 2, and indicate that $C_{16}$ and $C_{18}$ MES demonstrated superior detergency compared to shorter-length MES. As a result, $C_{16}$ and $C_{18}$, or a blend thereof, are the preferred MES components and formulations to provide superior detergency at relatively low concentrations.

Figure 3:
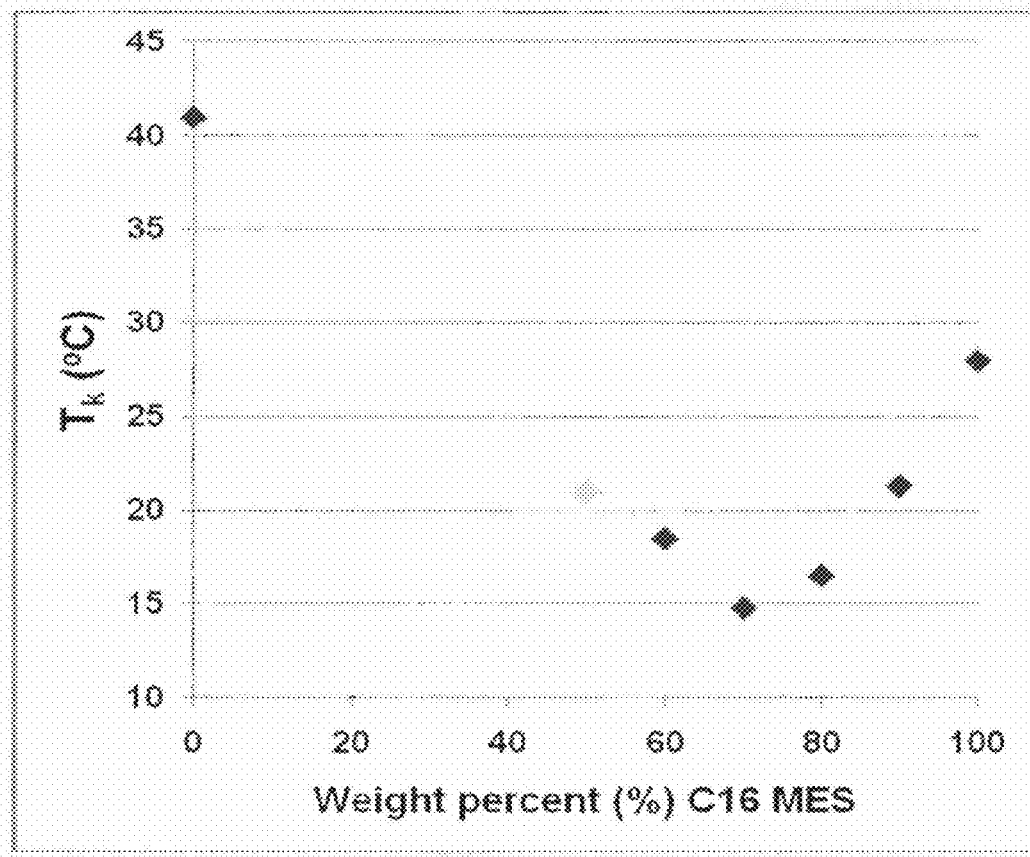
FIG. 3 is a scatter plot showing the effect of temperature of solution upon the solubility of 1% solution C16:C18 MES blends at increasing weight percent of the C16 MES in the blend.

We have also addressed the issue relating to solubility of MES, which impacts its suitability in aqueous-based household cleaning applications such as laundry and dish cleaning. It is known in the art that the MES forms that provide the best detergency (e.g., $C_{16}$ MES and $C_{18}$ MES, as noted above) also demonstrate decreasing water solubility. It is also known in the art, however, that blending chain lengths provides better water solubility than that of the pure components. For example, as reported in Schambil, F. and Schwuger, M. J., *Tenside Surf. Det.* 27: 380 (1990), which is incorporated by reference herein, certain mixtures of $C_{16}$ MES and $C_{18}$ MES are more soluble than either alone; the greatest solubility was observed with a $C_{16}$:$C_{18}$ ratio of 70:30 (w/w), which is referred to herein as eutectic MES or EMES due to the eutectic nature of the solubility of such blends (see FIG. 3). However, the work reported in this reference was performed using solutions of 1% total surfactant, which is far below the concentrations that are useful in household cleaning applications such as laundry and dish cleaning (which typically use between about 5% to about 15% (e.g., about 9%) surfactant concentrations).

Figure 4:
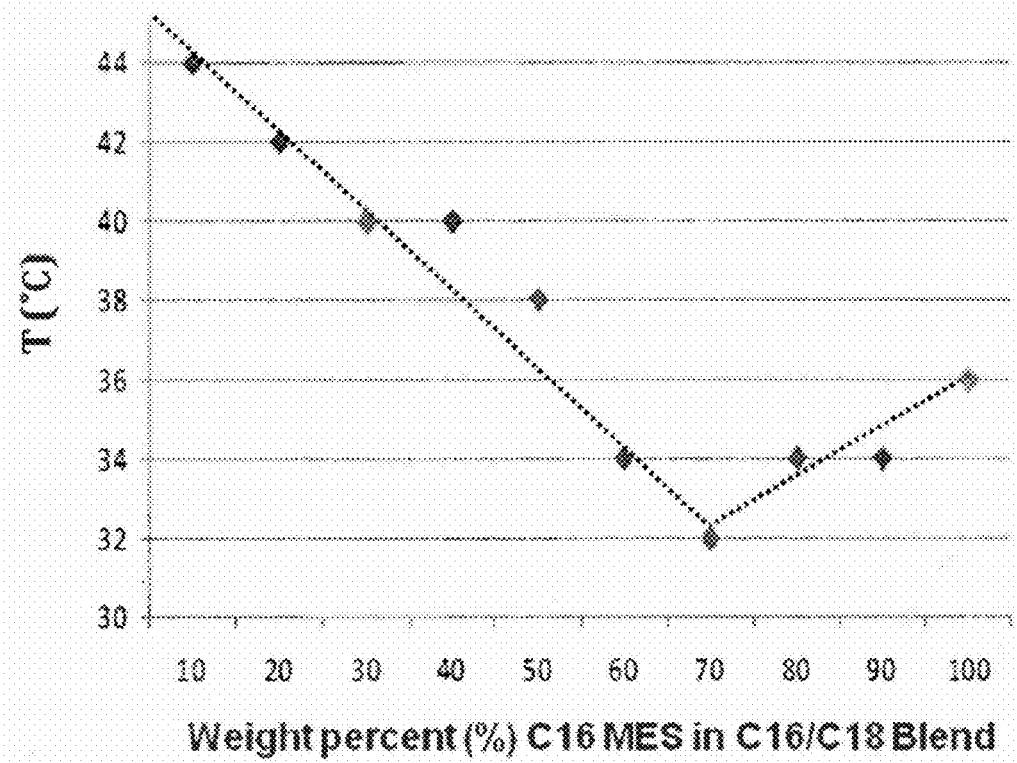
FIG. 4 is a line graph showing the effect of temperature of solution upon the solubility of 9% solution C16:C18 MES blends at increasing weight percent of the C16 MES in the blend.

We therefore wanted to examine the suitability of various surfactants, including eutectic methyl ester sulfonate (EMES) (i.e., a blend of $C_{16}$ MES:$C_{18}$ MES at a 70:30 ratio, w/w), for use in reducing surface tension over various surfactant concentrations. The studies noted above with 1% MES were repeated, testing concentrations of EMES up to a concentration of about 9% in water. The results of these studies, shown in FIG. 4, demonstrate that the eutectic behavior of MES holds at concentrations required for liquid laundry detergents (i.e., up to about 9% w/v). In fact, in these studies, we found that a ratio of 70:30 $C_{16}$ MES:$C_{18}$ (i.e., EMES) resulted in the optimal solubility profile, even at a total surfactant concentration of up to 9%.

Figure 5:
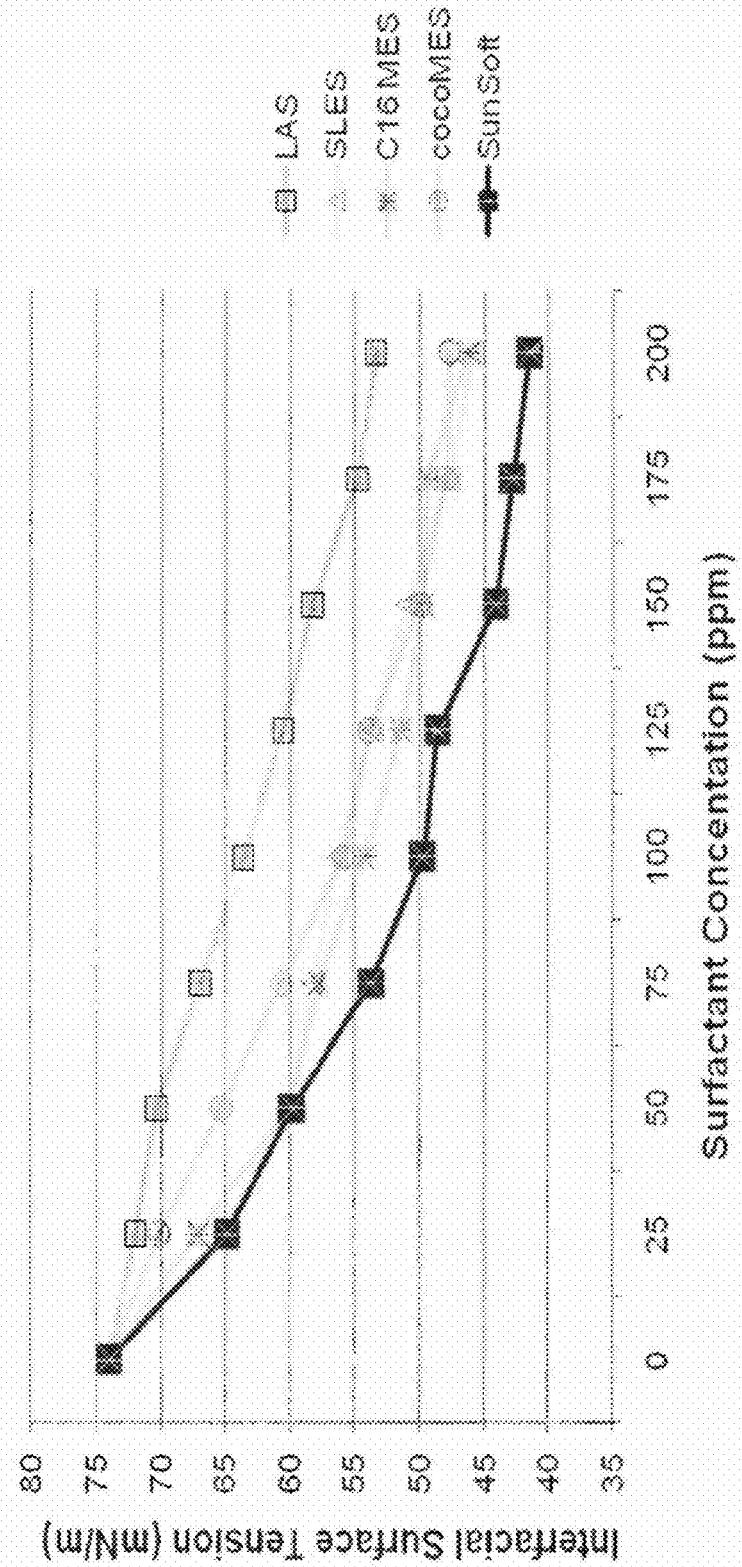
FIG. 5 is a line graph showing the interfacial surface tension of various anionic surfactants over increasing concentration. LAS: linear alkylbenzene sulfinate; SLES: sodium lauryl ether sulphate; C16 MES: methyl ester sulfonate (MES) having C16 alkyl fatty acid chains; cocoMES: MES having coco alkyl fatty acid chains; SunSoft™: a blend of C16 MES and C18 MES at a concentration ratio of C16:C18 of 70:30.

Finally, to examine the detergency of EMES compared to other surfactants (including other MES forms), we repeated the IFT/CMC studies noted above over a range of surfactant concentrations, again using the pendant drop method. The results of these experiments, shown in FIG. 5, demonstrate that amongst the surfactants, EMES (labelled as "SunSoft™" on FIG. 5) demonstrated the highest detergency (i.e., a more rapidly developing reduction in surface tension) at a relatively low CMC. Thus, we concluded that EMES is an ideal candidate surfactant for use in a variety of household cleaning applications, particularly in laundry detergent formulations.

Example 2

Improving the Solubility of EMES at High Concentrations and Low Storage and Use Temperatures Having determined that EMES is an ideal surfactant candidate, we next examined methods for addressing methods of overcoming the relatively poor solubility of MES surfactants at high concentrations and at low storage/use temperatures. Overcoming this problem would permit the production of laundry and dish cleaning formulations with higher concentrations of EMES (which would have concomitantly increased cleaning efficacy) while avoiding the precipitation, of the surfactant upon storage and use.

One of the most important aspects of developing an HDL (Heavy Duty Liquid) laundry detergent formulation is that it must be physically stable. A bottle of detergent may sit unused on a shelf for up to two years, and sometimes such products will be stored in a hot warehouse in summer or in an unheated garage during winter. For these reasons and to anticipate many other storage conditions that our products can encounter, any HDL formulation that is developed and implemented in the marketplace must meet several types of established storage stability criteria.

The following are the required storage temperatures and the duration that a sample must be tested at each temperature:

| Temperature (° F.) and test | Number of weeks of Storage |
| --- | --- |
| 125 | 1 |
| 105 | 12 |
| Room Temperature (70) | 52 |
| 40 | 12 |
| Freeze thaw | 3 cycling |
| Enzyme stability | 50% activity remaining after 52 weeks at room temperature |
| Enzyme stability | 50% activity remaining after 4 weeks at 37 C. |

The freeze thaw test was conducted by putting samples in a freezer at −20° C. and then thawing a sample at room temperature every two days. HDL formulations are required to pass 1 week of freeze/thaw storage, which is equivalent to 3 freeze/thaw cycles.

Samples were checked periodically throughout storage stability testing and visually examined for any evidence of precipitation or separation. A stability test schedule for HDLs follows at the end of this procedure. Where an 'X' is marked, the samples are removed from their chambers or ovens and examined. At this time, observations are recorded on a storage record or storage sheet. After the storage in each temperature is completed, the sample should be disposed of. In addition, the minimum Pass/Fail stability requirements for HDLs are listed in the last column of this table.

Fragrance stability was also checked with the final fragrance:

| Temperature (° F.) and test | Number of weeks of Storage |
| --- | --- |
| 105 physical stability | 4 |
| 105 olfactive stability | 4 |
| 105 base odor olfactive profile | 4 |
| Without fragrance | |

Sample Preparation:

After a formulation was completed and ready for storage stability testing, the required number of jars, caps and labels were prepared; storage data sheets were also prepared. Note: HDL products could be stored in 2-ounce glass jars or 4-ounce plastic jars; formulas containing silicate builders, however, should not use glass jars. Each jar should be at least ½ to ¾ full and labelled. Upon being filled with samples, the jars were placed into the appropriate storage condition, and the storage number of each sample was recorded on the storage stability sheet.

Sample Evaluation and Recording Observations:

Samples were removed from oven when required (according to the schedule noted below and on the storage data sheet), and placed onto a countertop. Samples were allowed to sit for about four (4) hours so that they reached room temperature. Following cooling, the samples were visually observed and carefully examined, looking for evidence of instability by noting the presence of any of the following: precipitation, suspended material, separation of phases, gel formation, discoloration, haziness and cloudiness/opacity. During evaluation, the samples were gently turned over to view the bottom portion of the sample or to look for precipitation. Observations were recorded on the sample data sheets; in general, any departure from the product's normal appearance was noted, and evidence of any of the instabilities listed above (i.e., any evidence that the solution was not a clear, isotropic liquid) was noted and described in some detail.

| HEAVY DUTY LIQUIDS (HDL) PHYSICAL STABILITY TEST DESIGN AND SCHEDULE | | | | | | | | |
| --- | --- | --- | --- | --- | --- | --- | --- | --- |
| | Week | | | | | | | |
| Temperature (° F.) | 1 | 2 | 4 | 8 | 12 | 26 | 52 | Pass/Fail |
| 125 | X | | | | | | | |
| 105 | X | X | X | X | X | | | |
| RT | | | X | X | X | X | X | |
| 40 | X | X | X | X | X | | | |
| Freeze thaw, 3 cycles | X | | | | | | | |
| Enzyme stability 37 C. | X | X | X | | | | | |

Similar approaches were taken for examining the impact of increasing EMES concentration on liquid stability (i.e., examining the solubility of the surfactant in solution at a given concentration), and the ability of hydrotropes to improve EMES solubility. Specifically, samples of EMES in water were prepared at different concentrations and observed as described above for any evidence of instability or poor solubility.

Figure 6:
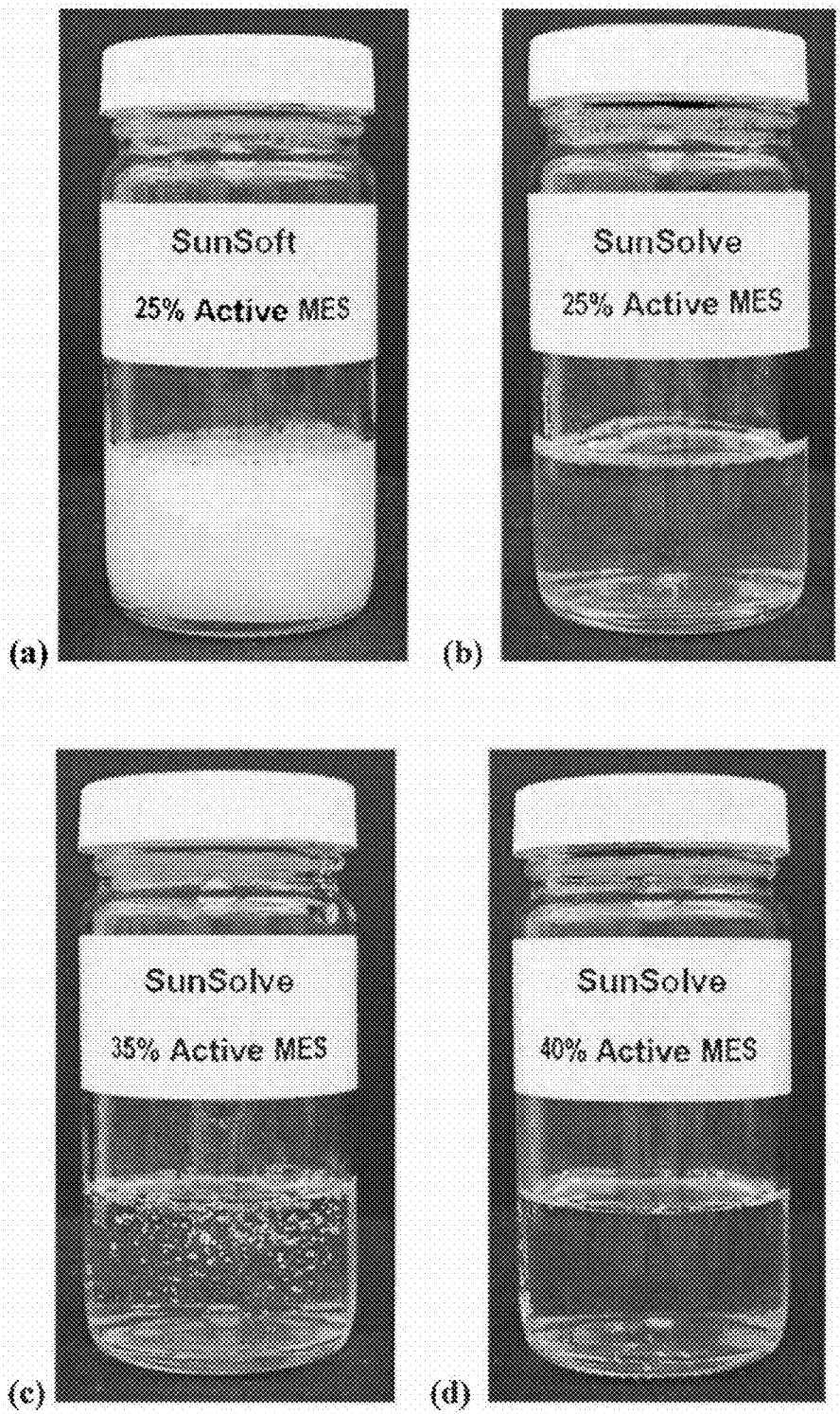
FIG. 6 is a series of photographs of glass bottles containing MES solutions at various concentrations, showing the impact of the inclusion of 2%-7% hydrotrope on the solubility of the MES.

As shown in FIG. 6, at a concentration of 25% in water, EMES (SunSolve™) is very poorly soluble (FIG. 6*a*). In fact, as noted above, EMES is poorly soluble at concentrations above about 10-15%. However, the inclusion of as little as about 2% $C_8$ amine oxide ($C_8$ AO) in the solution renders a nearly clear, isotropic solution of EMES at a surfactant concentration of 25% (FIG. 6b; "SunSoft™"). Indeed, this level of $C_8$ AO was found to stabilize solutions of EMES at surfactant concentrations of 35% (FIG. 6c) and 40% (FIG. 6d). Concentrations of EMES at even higher than 40% have also been found to be stabilized by the inclusion of about 2% to about 7% $C_8$ AO (data not shown). Optimal results were obtained with a solution containing about 35% EMES and from about 2% to about 7% $C_8$ AO. These results demonstrate that by including the proper levels of a selected hydrotrope, high-concentration EMES solutions that are stable (i.e., that form and remain as an isotropic liquid) can be prepared.

To determine other potentially suitable hydrotropes that may be useful in maintaining stability of high-concentration EMES solutions over a range of temperatures, we evaluated over 150 candidate materials. These included the following:

| Trade Name | Supplier | Description |
| --- | --- | --- |
| Amine Oxides | | |
| Lonza FMB AO-8 | Lonza | C8 AO |
| Stepan Agent 3785-87 | Stepan | Synth C8 AO |
| Ammonyx 810 DO 3494-19 | Stepan | C8-10 Blend |
| Synthetic C8 3853-01 | Stepan | Natural C8 AO |
| Genaminox OC | Clariant | C8 AO |
| Genaminox 1014 | Clariant | C10-14 |
| Genaminox DC40 | Clariant | C10 AO |
| Mackamine C8 | Rhodia | C8 AO |
| Ammonyx | Stepan | C-12 Amine Oxide |
| Macat AO-8 | Mason Chem. | C-8 Amine Oxide |
| Caloxamine CPO | Pilot Chemical | Cocamidopropylamine Oxide |
| Other Materials | | |
| AlphaStep MC-48 | Stepan | |
| AlphaStep PC-48 | Stepan | |
| Tomamine LH | Air Products | Amphoteric Surfactant (Natural) |
| Tomadol 900 | Air Products | |
| Tween 20 | Croda | Polysorbate 20 |
| Glucopon 220 UP | Cognis | APG |
| AG6206 | Akzo | |
| Mackam CBS-50G | Rhodia McIntyre | Cocamidopropyl hydroxy sultaine |
| Mackam 2CSF-40CG | Rhodia McIntyre | disodium cocoamphodipropionate |
| Mackam 35 | Rhodia McIntyre | Coco betaine |
| Mackam CB-35 | Rhodia McIntyre | Coco betaine |
| TEA | | Hydrotrope |
| Sodium Xylene Sulfonate | | Hydrotrope |
| Glycerine | | Hydrotrope |
| Propylene Glycol | | Hydrotrope |
| Ethanol | | Hydrotrope |
| DeTerg 2417-J | DeForrest | |
| DeTerg 2417-IMOD | DeForrest | |
| DeTerg 2417-I | DeForrest | |
| DeTerg 2417-H | DeForrest | |

Samples of EMES with about 2% of these or other potential hydrotropes were prepared and subjected to temperature stability testing as noted above. Samples were evaluated on a "Pass/Fail" basis; a sample was said to "Pass" if it remained a clear isotropic liquid at the indicated challenge temperature, while a sample was said to "Fail" if it showed any of the above-described evidence of instability or insolubility. For a given candidate material, "Fail" indicates that the material provided no benefit to solubilization or stability of EMES at the indicated concentration and temperature, while "Pass" indicates that the material showed a benefit to solubilization of EMES at the indicated concentration and temperature.

Materials were evaluated each at 2% (w/v), unless otherwise noted below, by inclusion in a base liquid detergent formulation containing the following components:

| | |
| --- | --- |
| Water | 51.349% |
| Citric Acid | 2.000% |
| Caustics | 1.400% |
| Triethanolamine | 2.000% |
| LAS | 1.500% |
| EMES | 9.500% |
| AWC | 3.000% |
| 24-7 | 17.000% |
| PLX | 0.150% |
| IDS | 0.500% |
| TSA | 0.500% |
| LG | 0.001% |
| Amylase | 0.100% |
| Protease | 3.000% |
| Hole | 8.000% |

Results were as follows:

| Material | Chemical Name | Amt. (% w/v) | 40° F. storage | 105° F. storage | 125° F. storage | Freeze/ Thaw storage | Room Temp. storage |
| --- | --- | --- | --- | --- | --- | --- | --- |
| Lonza FMB AO-8 | Octyl dimethyl amine oxide | 2.00 | Pass | Pass | Pass | Pass | Pass |
| Stepan Agent 3785-87 | Octyl dimethyl amine oxide | 2.00 | Pass | Pass | Pass | Pass | Pass |
| Ammonyx 810 DO 3494-19 | Octyl/decyl dimethyl amine oxide | 2.00 | Fail | Pass | Pass | Pass | Pass |
| Synthetic C8 3853-01 | Octyl dimethyl amine oxide | 2.00 | Pass | Pass | Pass | Pass | Pass |
| Genamino x OC | Octyl dimethyl amine oxide | 2.00 | Pass | Pass | Pass | Pass | Pass |
| Genamino x 1014 | C10 alkyl dimethyl amine oxide and C14 alkyl dimethyl amine oxide blend | 2.00 | Fail | Pass | Pass | Pass | Pass |
| Genamino x DC40 | Decyl dimethyl amine oxide | 2.00 | Fail | Pass | Pass | Pass | Pass |

-continued

| Material | Chemical Name | Amt. (% w/v) | 40° F. storage | 105° F. storage | 125° F. storage | Freeze/ Thaw storage | Room Temp. storage |
|---|---|---|---|---|---|---|---|
| Mackamine C8 | Octyl amine oxide | 2.00 | Pass | Pass | Pass | Pass | Pass |
| Ammonyx LO | Lauramine oxide | 2.00 | Fail | Pass | Pass | Pass | Pass |
| Macat AO-8 | Octyl dimethyl amine oxide | 2.00 | Pass | Pass | Pass | Pass | Pass |
| Caloxamine CPO | Cocamidopropyl amine oxide | 2.00 | Fail | Pass | Pass | Pass | Pass |
| Aramox C-12 | Bis (2-hydroxyethyl) cocoalklyamine oxide | 2.00 | Fail | Pass | Pass | Pass | Pass |
| Aramox APA-TW | Tallow alkylamido propyl dimethyl amine oxide | 2.00 | Fail | Pass | Pass | Pass | Pass |
| Barlox 10-S | Decyl dimethyl amine oxide | 2.00 | Fail | Pass | Pass | Pass | Pass |
| Cocamidopropyl betaine | Cocamidopropyl betaine | 2.00 | Fail | Pass | Pass | Pass | Pass |
| AlphaStep MC-48 | Sodium alphasulfomethyl C12-18 ester & disodium alphasulfo C12-18 fatty acid salt | 2.00 | Fail | Pass | Pass | Pass | Pass |
| AlphaStep PC-48 | Sodium methyl-2-sulfo C12-C18 ester & disodium 2-sulfo C12-C18 fatty acid | 2.00 | Fail | Pass | Pass | Pass | Pass |
| Tomamine LH | Betaine | 2.00 | Fail | Pass | Pass | Pass | Pass |
| Tomadol 900 | Non-ionic surfactant avg. C9 (blend C9, 11-12-15) | 2.00 | Fail | Pass | Pass | Pass | Pass |
| Tween 20 | Polysorbate 20 | 2.00 | Fail | Pass | Pass | Pass | Pass |
| Glucopon 220 UP | Alkylpolyglucoside | 2.00 | Fail | Pass | Pass | Pass | Pass |
| AG6206 | Akkylglucoside | 2.00 | Fail | Pass | Pass | Pass | Pass |
| Mackam CBS-50G | Cocamidopropyl hydroxysultaine | 2.00 | Fail | Pass | Pass | Pass | Pass |
| Mackam 2CSF-40CG | Disodium cocaphodia propionate | 2.00 | Fail | Pass | Pass | Pass | Pass |
| Mackam 35 | Cocamidopropyl betaine | 2.00 | Fail | Pass | Pass | Pass | Pass |
| Mackam CB-35 | Coco betaine | 2.00 | Fail | Pass | Pass | Pass | Pass |
| TEA | Triethanolamine | 3.00 | Fail | Pass | Pass | Pass | Pass |
| TEA | Triethanolamine | 4.00 | Fail | Pass | Pass | Pass | Pass |
| TEA | Triethanolamine | 5.00 | Fail | Pass | Pass | Pass | Pass |
| Sodium xylene sulfonate | Sodium xylene sulfonate | 2.00 | Fail | Pass | Pass | Pass | Pass |
| Glycerine | Glycerine (propane 1,2,3-triol) | 2.00 | Fail | Pass | Pass | Pass | Pass |
| Propylene glycol | Propylene glycol (1,2-propane diol) | 2.00 | Fail | Pass | Pass | Pass | Pass |
| Ethanol | Ethyl alcohol | 2.00 | Fail | Pass | Pass | Pass | Pass |

Figure 7:
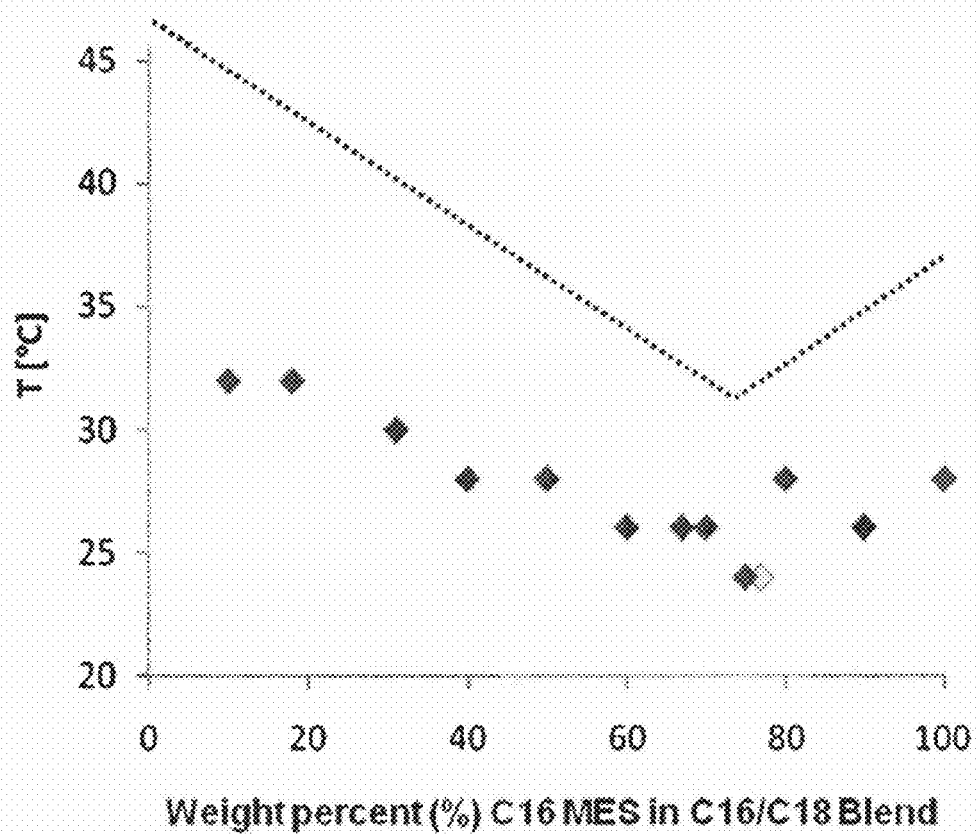
FIG. 7 is a line graph showing the effect of temperature of solution upon the solubility of 9.5% solution C16:C18 MES blends and 2% C8 amine oxide, at increasing weight percent of the C16 MES in the blend.
Figure 8:
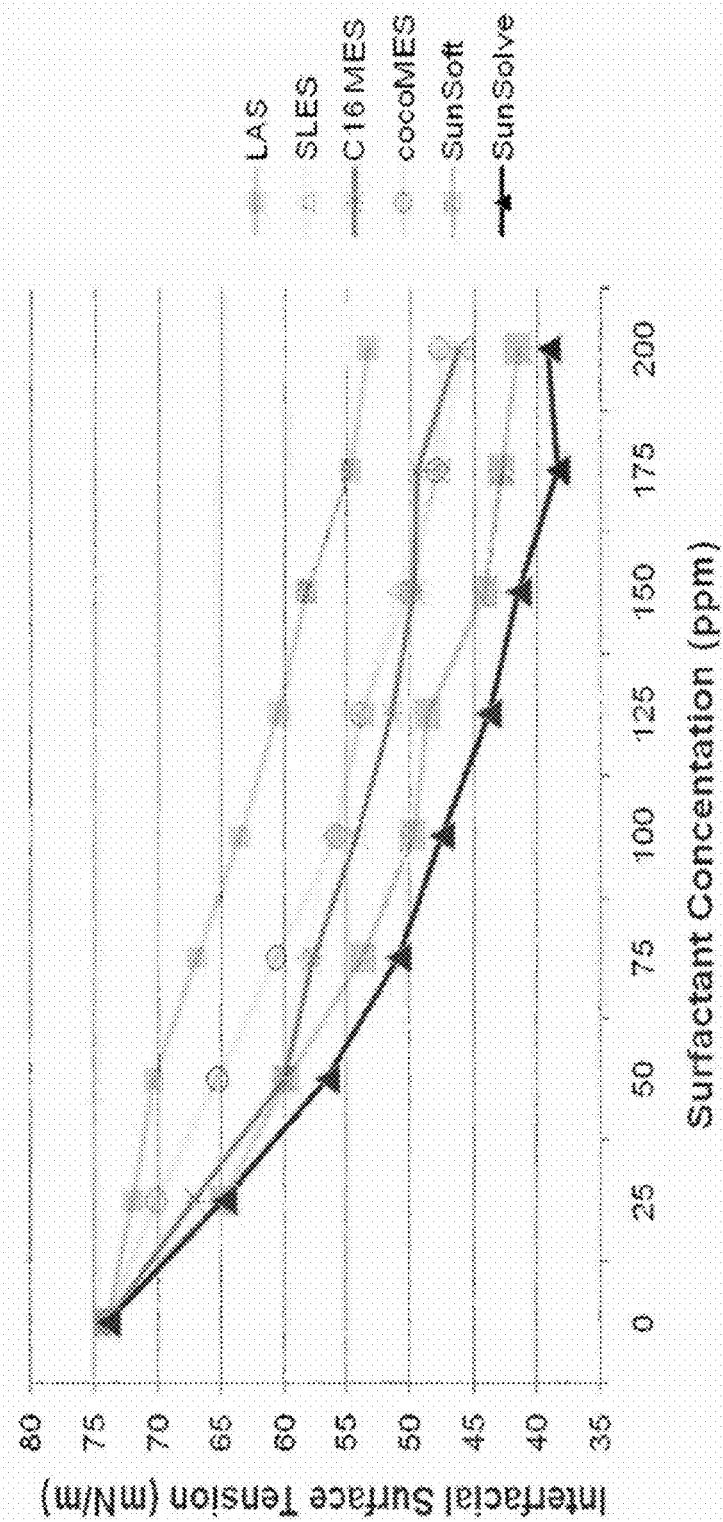
FIG. 8 is a line graph showing the interfacial surface tension of various anionic surfactants over increasing concentration. LAS: linear alkylbenzene sulfonate; SLES: sodium lauryl ether sulphate; C16 MES: methyl ester sulfonate (MES) having C16 alkyl fatty acid chains; cocoMES: MES having coco alkyl fatty acid chains; SunSoft™: a blend of C16 MES and C18 MES at a concentration ratio of C16:C18 of 70:30; SunSolve™: SunSoft™ MES blend with the addition of about 2% C8 amine oxide.

These results demonstrate that a number of potentially hydrotropic materials can be used to solubilise EMES at relatively high concentrations (e.g., at about 9.5%). Importantly, however, most of the tested materials did not provide stability of EMES formulations at lower temperatures (e.g., at 40° F.); at these temperatures, only octyl (i.e., C8) amine oxides demonstrated the ability to maintain the formulations as a clear isotropic liquid. Similar results were obtained for solutions containing concentrations of EMES at higher than about 9.5% over a variety of temperatures, as shown in FIG. 7. Moreover, the inclusion of amine oxide in high-concentration EMES formulations ("SunSolve™") was found to improve even further the detergency of the formulation when compared to other surfactant systems or even to EMES formulations without amine oxide ("SunSoft™"), as shown in FIG. 8. Taken together, these results show that for cold temperature storage or use (e.g., in cold water washing), or even for long-term storage, EMES-containing formulations should be formulated with at least about 2% C8 amine oxide so as to maintain the stability and detergency of the EMES components. Such formulations ("SunSolve™") are available from The Sun Products Corporation, Wilton, Conn.

Example 3

Flowability of High-Concentration EMES Formulations

For certain cleaning applications (e.g., personal care, laundry stain pre-treatment), it may be desirable to have a pumpable detergent formulation. We therefore examined whether or not high-concentration EMES formulations remained sufficiently flowable to be suitable for use with a pump delivery device or container.

Figure 9:
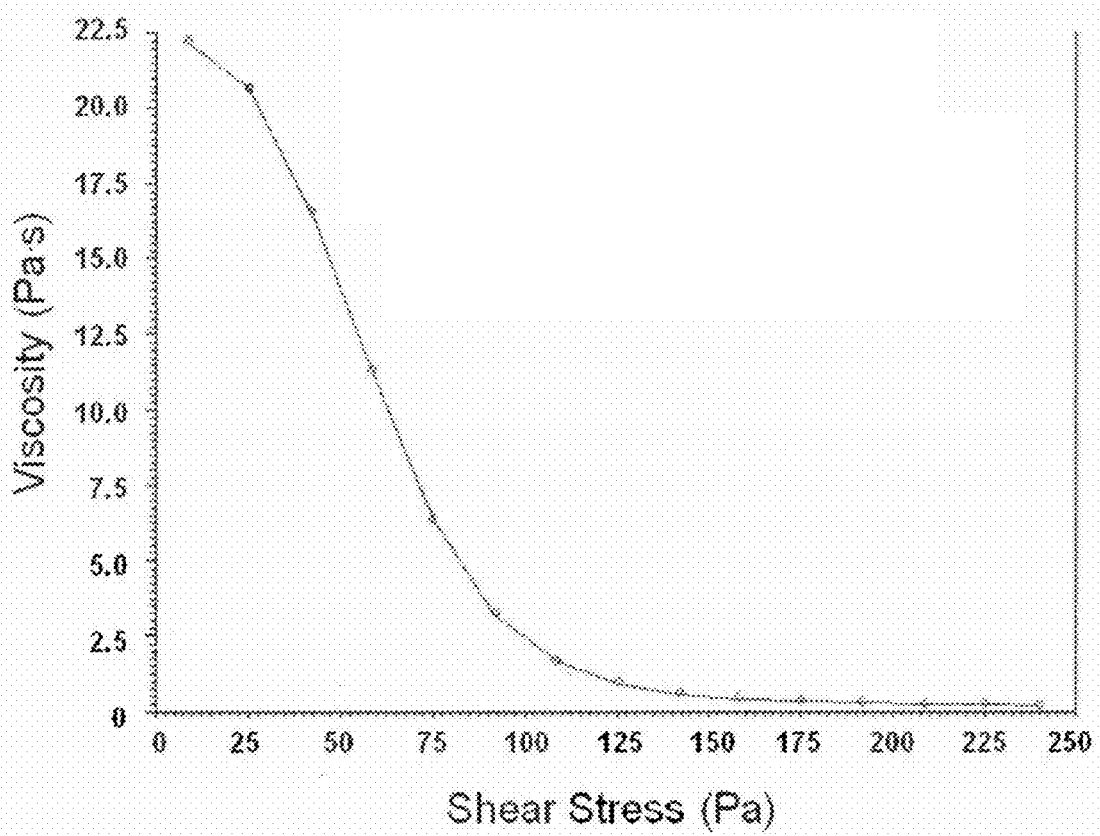
FIG. 9 is a line graph showing the effect of shear stress upon the viscosity of a 35% solution of SunSoft™ EMES.

A solution of 35% EMES+7% C8 amine oxide in water was prepared as described in the foregoing examples. This solution was found to flow, albeit very slowly. The rheology of the solution was then tested using a 40 mm circular plate rheometer. A conditioning step was performed which brought the plate to 25° C., and a pre-shear step was carried out at 0.7958 Pa for 30 sec, and then the device was equilibrated until it reached 0 velocity. Then the main continuous ramp step began on the solution, which ran for 1 minute, and the shear stress was increased from 0.1 to 250 Pa. A total of 15 data points were collected, and the device remained at 25° C. the entire time. Results are shown in FIG. 9. These results demonstrated that the solution of 35% EMES/7% C8 amine oxide was shear-thinning and was pumpable. With increasing shear stress, the viscosity of the solution was found to drop significantly. At a shear stress of 175 Pa, the viscosity of the solution was found to be a mere 330 cP, which did not create a barrier to pumpability of the solution. Solutions of about 40% or more EMES, however, required a slightly higher amine oxide content to remain flowable and pumpable, but the shear stress necessary was inordinately high. Therefore, for applications in which it may be desirable to pump the surfactant formulation, it is preferable to use 35% or lower EMES in the formulation.

We also evaluated whether or not inclusion of one or more additional components in the solution would improve the pumpability of high concentration EMES formulations. Specifically, ethanol or glycerine at about 5% to about 8% were included in formulations containing 35% EMES/7% C8 amine oxide. The results of these studies (not shown) demonstrated that not only did the inclusion of these agents in the formulations improve flowability/pumpability of the solutions—in fact, the flowability was worse than without the inclusion of these agents.

Example 4

Suitability of EMES Formulations in Hard Water Environments

In certain environments and even neighbourhoods, or in households in which well water is used, high ionic content (i.e., hardness) of the water can be detrimental to the cleaning performance of detergent formulations. For example, the presence of hardness ions has a dramatic negative impact on stain removal performance with LAS/SLES-based detergents.

We therefore wanted to examine the impact of water hardness on the cleaning performance of EMES-based detergent formulations.

EMES formulations were prepared as described above and compared to traditional LAS/SLES-based laundry detergent formulations under standard domestic washing conditions. Tests were performed in standard top load washing machines (US) using mixed ballast (2.7 kg) in 68 L wash liquor using a 48 g/load dose of the formulation. Tests were performed at warn (32° C.) and cold (15° C.) water conditions, and at water hardness levels of 0 and 300 ppm. Standard test stains were prepared according to ASTM standards or other art-known methods, and detergency was determined by examining the stain levels (via spectrophotometry) after washing vs. a control, unwashed stain swatch. To determine the impact of water hardness on detergency, stain removal results for a given formulation at a given temperature on a given stain at 0 ppm water hardness were compared to those at 300 ppm water hardness, and the difference at 300 ppm expressed as relative decrease in detergency.

Figure 10:
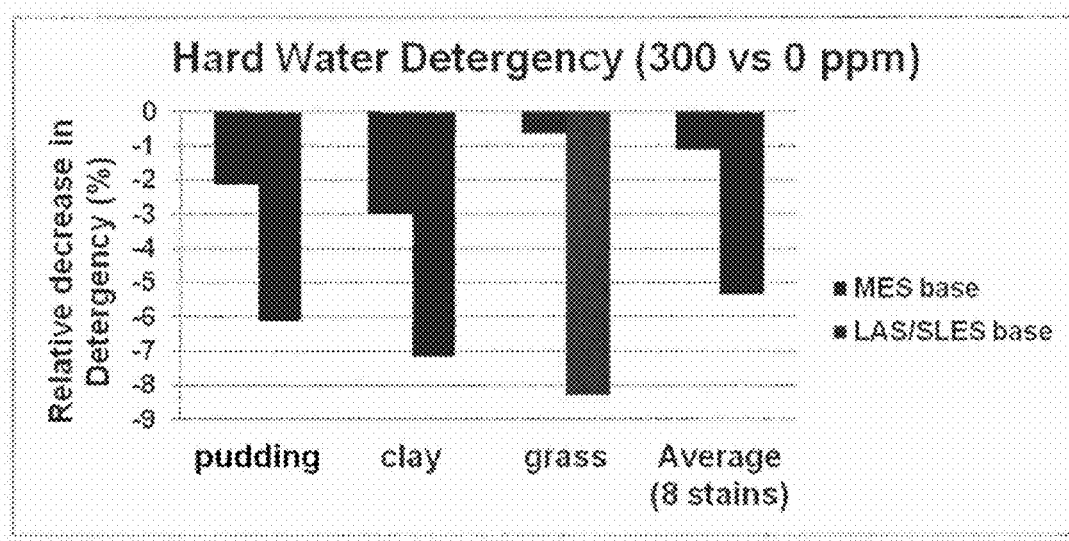
FIG. 10 is a bar graph showing the superior detergency performance in hard water of SunSoft™ EMES (MES base) vs. traditional laundry detergent formulations (LAS/SLES base) on a variety of stain types.

As shown in FIG. 10, harder water dramatically affected the detergency of LAS/SLES-based formulations, while the impact on detergency of the EMES-containing formulations was significantly lower. While there was some difference in overall cleaning effectiveness amongst different stain types within a given formulation, overall the EMES-containing formulations retained significantly higher detergency in hard water conditions relative to traditional laundry detergent formulations. This difference was found to be true at both of the washing temperatures tested (data not shown). These results demonstrate that for maximum detergency and cleaning effectiveness across a range of water hardness, EMES-containing formulations such as those of the present invention are preferred over traditional detergent formulations.

Example 5

Measurement of Skin Irritation Caused by Surfactant Formulations

For certain applications, such as use in hand dish cleaning formulations, it is desirable that the surfactant(s) used not be irritating to skin. We therefore evaluated the level of skin irritation of various surfactant formulations, including a 2% MES formulation, using the zein solubilisation method (see, e.g., Zoller, U., *CRC Handbook of Detergents, Part E: Applications, Part 2*, section 3.2.2.3, pages 47-48 (2008; CRC Press, Boca Raton, Fla.; which is incorporated herein by reference).

Figure 11:
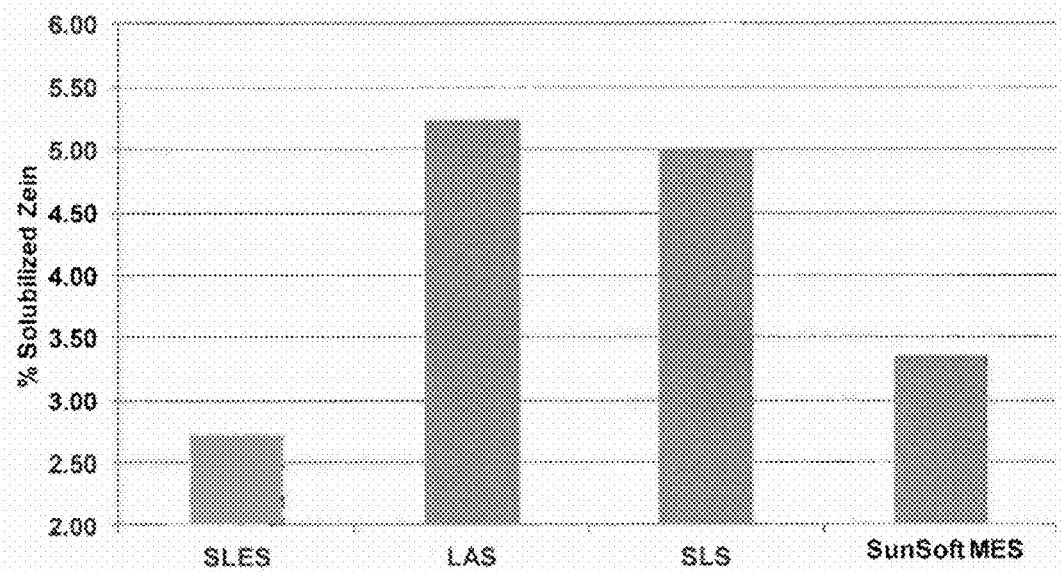
FIG. 11 is a bar graph depicting the results of zein solubilisation analysis, an in vitro model of skin harshness, for 2% solutions of various surfactant-containing formulations. SLES: sodium lauryl ether sulphate; LAS: linear alkylbenzene sulfonate; SLS: sodium lauryl sulphate; SunSoft™ MES: a blend of C16 MES and C18 MES at a concentration ratio of C16:C18 of 70:30.

As shown in FIG. 11, SunSoft™ EMES was found to be less irritating to skin than other common anionic surfactants such as SLS and LAS. Thus, SunSoft™ EMES (and, likely, MES in general) should be considered an excellent surfactant for use in hand washing in both laundry and dish applications, and may also have applications in other skin-sensitive formulations such as in personal care.

Having thus described in detail the preferred embodiments of the present invention, it is to be understood by those of ordinary skill in the art that the same can be performed within a wide and equivalent range of conditions, formulation and other parameters without affecting the scope of the invention or any embodiments thereof. All patents, patent applications and publications cited herein are fully incorporated by reference in their entirety.

What is claimed is:

1. A liquid composition, comprising:
    about 0.5% to about 50% by weight of the composition of a blend of $C_{16}$ and $C_{18}$ α-sulfofatty acid methyl ester, wherein the blend is at a concentration ratio of C16:C18 of about 50:50 to about 70:30; and
    about 0.5% to about 10% by weight of the composition of a $C_8$ alkyl dimethyl amine oxide.

2. The composition of claim 1, wherein the blend of the $C_{16}$ α-sulfofatty acid methyl ester and the $C_{18}$ α-sulfofatty acid methyl ester is at a concentration ratio of $C_{16}$:$C_{18}$ of about 70:30.

3. The composition of claim 1 or 2, wherein the composition is enriched for the $C_{16}$ α-sulfofatty acid methyl ester.

4. The composition of claim 1, wherein said composition comprises about 5% to about 40% by weight of the composition of the blend of $C_{16}$ and $C_{18}$ α-sulfofatty acid methyl esters.

5. The composition of claim 1, wherein said composition comprises about 1% to about 5% by weight of the composition of the $C_8$ alkyl dimethyl amine oxide.

6. The composition of claim 5, wherein said composition comprises about 1.5% to about 3% by weight of the composition of the $C_8$ alkyl dimethyl amine oxide.

7. The composition of claim 1, wherein the blend of $C_{16}$ α-sulfofatty acid methyl ester and $C_{18}$ α-sulfofatty acid methyl ester, is at a concentration ratio of $C_{16}:C_{18}$ of about 70:30, at a concentration of the blend of about 25% to about 40% of the weight of the composition.

8. The composition of claim 7, wherein the concentration of the blend in the composition is about 25% of the weight of the composition.

9. The composition of claim 7, wherein the concentration of the blend in the composition is about 30% of the weight of the composition.

10. The composition of claim 7, wherein the concentration of the blend in the composition is about 35% of the weight of the composition.

11. The composition of claim 7, wherein the concentration of the blend in the composition is about 40% of the weight of the composition.

12. The composition of claim 7, wherein the concentration of the blend in the composition is about 45% of the weight of the composition.

13. The composition of claim 1, wherein the blend of $C_{16}$ α-sulfofatty acid methyl ester and $C_{18}$ α-sulfofatty acid methyl ester is at a concentration ratio of $C_{16}:C_{18}$ of about 70:30, at a concentration of the blend of about 25% to about 40% of the weight of the composition, and wherein said composition comprises the $C_8$ alkyl dimethyl amine oxide at a concentration in the composition of from about 2% to about 7% by weight of the composition.

14. The composition of claim 13, wherein the blend of $C_{16}$ α-sulfofatty acid methyl ester and $C_{18}$ α-sulfofatty acid methyl ester is present in the composition at a concentration of about 35% by weight of the composition, and wherein the $C_8$ alkyl dimethyl amine oxide is present in said composition at a concentration in the composition of about 7% by weight of the composition.

15. The composition claim 1, wherein the composition is formulated for use at a temperature of less than about 30° C.

16. The composition claim 15, wherein the composition is formulated for use at a temperature of less than about 20° C.

17. The composition of claim 16, wherein the composition is formulated for use at a temperature of less than about 10° C.

18. The composition of claim 1, further comprising a nonionic surfactant, an other anionic surfactant, a cationic surfactant, a zwitterionic surfactant, a polymer dispersant, a builder, an oxidizing agent, a biocidal agent, a foam regulator, an activator, a catalyst, a thickener, a fragrance, a soil suspending agent, a brightener, an enzyme, a UV protector, a salt, water, or an inert ingredient.

19. The composition of claim 1, wherein the composition is contained in a water soluble container.

20. The composition of claim 19, wherein the water soluble container is or comprises a polyvinylalcohol film.

21. The composition of claim 1, wherein said composition is formulated as a laundry detergent composition suitable for use in laundering fabrics.

22. The composition of claim 1, wherein said composition is formulated as a dish detergent formulation suitable for use in cleaning dishware.

23. The composition of claim 22, wherein said dish detergent formulation is suitable for use in an automatic dishwashing machine.

24. The composition of claim 22, wherein said dish detergent formulation is suitable for use in hand washing of dishware.

25. The composition of claim 1, wherein said composition is formulated as a detergent formulation suitable for use in cleaning a household hard surface.

26. The composition of claim 1, wherein said composition is formulated as a detergent formulation suitable for use in personal care cleaning.

27. The composition of claim 26, wherein said composition is a shampoo formulation or a body wash formulation.

28. A method of laundering a fabric comprising contacting a water solution comprising the fabric with the composition of claim 1 or claim 21.

29. A method of cleaning dishware comprising contacting the dishware with a water solution comprising the composition of claim 1 or claim 22.

30. A method of cleaning a household hard surface comprising contacting the hard surface with a water solution comprising the composition of claim 1 or claim 25.

31. A method of personal care cleaning comprising washing a part of a human body with the composition of claim 1 or claim 26.

32. The method of claim 28, wherein said water solution is at a temperature of 50° F. or lower.

33. The method of claim 28, wherein said water solution is at a temperature of 40° F. or lower.

34. The method of claim 29, wherein said water solution is at a temperature of 50° F. or lower.

35. The method of claim 29, wherein said water solution is at a temperature of 40° F. or lower.

36. The method of claim 30, wherein said water solution is at a temperature of 50° F. or lower.

37. The method of claim 30, wherein said water solution is at a temperature of 40° F. or lower.

38. The method of claim 31, wherein said water solution is at a temperature of 50° F. or lower.

39. The method of claim 31, wherein said water solution is at a temperature of 40° F. or lower.

* * * * *